(12) United States Patent
Buckler et al.

(10) Patent No.: US 11,257,584 B2
(45) Date of Patent: Feb. 22, 2022

(54) QUANTITATIVE MEDICAL IMAGING REPORTING

(71) Applicant: Elucid Bioimaging Inc., Boston, MA (US)

(72) Inventors: Mary E. Buckler, Wenham, MA (US); Xiaonan Ma, South Hamilton, MA (US); Lawrence Martell, Wenham, MA (US); Andrew J. Buckler, Boston, MA (US)

(73) Assignee: ELUCID BIOIMAGING INC., Boston, MA (US)

( * ) Notice: Subject to any disclaimer, the term of this patent is extended or adjusted under 35 U.S.C. 154(b) by 81 days.

(21) Appl. No.: 16/102,042

(22) Filed: Aug. 13, 2018

(65) Prior Publication Data

US 2019/0074082 A1 Mar. 7, 2019

Related U.S. Application Data

(60) Provisional application No. 62/544,298, filed on Aug. 11, 2017.

(51) Int. Cl.
| | |
|---|---|
| *G06F 40/30* | (2020.01) |
| *G16H 50/20* | (2018.01) |
| *G16H 30/20* | (2018.01) |
| *G06F 16/36* | (2019.01) |
| *G06F 16/332* | (2019.01) |

(Continued)

(52) U.S. Cl.
CPC ......... *G16H 30/20* (2018.01); *G06F 16/3329* (2019.01); *G06F 16/367* (2019.01); *G06F 40/30* (2020.01); *G06T 7/0012* (2013.01);

*G16H 50/20* (2018.01); *G06F 40/211* (2020.01); *G06F 40/242* (2020.01); *G06F 40/284* (2020.01); *G16H 15/00* (2018.01)

(58) Field of Classification Search
CPC ...... G06F 40/211; G06F 40/284; G06F 40/30; G06F 16/3329; G16H 10/20; G16H 15/00; G16H 30/20; G16H 50/20
See application file for complete search history.

(56) References Cited

U.S. PATENT DOCUMENTS

| | | | |
|---|---|---|---|
| 6,108,635 A | 8/2000 | Herren et al. | |
| 6,416,476 B1 * | 7/2002 | Ogasawara | A61B 8/00 600/425 |

(Continued)

FOREIGN PATENT DOCUMENTS

| | | |
|---|---|---|
| EP | 1810185 | 7/2007 |
| WO | 2015058151 A2 | 4/2015 |

OTHER PUBLICATIONS

Aerts, H.J.W.L., et al., Decoding tumour phenotype by noninvasive imaging using a quantitative radiomics approach. Nat Commun, 2014. 5.

(Continued)

*Primary Examiner* — Lamont M Spooner
(74) *Attorney, Agent, or Firm* — Pearl Cohen Zedek Latzer Baratz LLP

(57) ABSTRACT

Advanced reporting systems based on ontology development for quantitative imaging biomarkers, information modeling to integrate heterogeneous data types relevant to quantitative medical analysis, and a knowledge representation framework for their statistical validation.

23 Claims, 19 Drawing Sheets

(51) Int. Cl.
*G06T 7/00* (2017.01)
*G06F 40/211* (2020.01)
*G06F 40/242* (2020.01)
*G06F 40/284* (2020.01)
*G16H 15/00* (2018.01)

(56) References Cited

U.S. PATENT DOCUMENTS

| | | | | |
|---|---|---|---|---|
| 6,675,033 | B1* | 1/2004 | Lardo | G01R 33/287 |
| | | | | 324/300 |
| 7,793,217 | B1 | 9/2010 | Kim et al. | |
| 10,646,160 | B2* | 5/2020 | Yelin | A61B 5/0066 |
| 2001/0056232 | A1* | 12/2001 | Lardo | G01R 33/34053 |
| | | | | 600/423 |
| 2002/0045816 | A1* | 4/2002 | Atalar | G01R 33/285 |
| | | | | 600/423 |
| 2002/0103776 | A1 | 8/2002 | Bella et al. | |
| 2003/0028095 | A1* | 2/2003 | Tulley | G01R 33/3657 |
| | | | | 600/422 |
| 2003/0105638 | A1 | 6/2003 | Taira | |
| 2005/0043614 | A1 | 2/2005 | Huizenga et al. | |
| 2005/0118632 | A1 | 6/2005 | Chen et al. | |
| 2005/0245814 | A1* | 11/2005 | Anderson | G01R 33/287 |
| | | | | 600/410 |
| 2006/0242288 | A1 | 10/2006 | Masurkar | |
| 2007/0026525 | A1* | 2/2007 | Marcelpoil | G06T 7/0012 |
| | | | | 436/63 |
| 2007/0130206 | A1 | 6/2007 | Zhou et al. | |
| 2007/0208516 | A1 | 9/2007 | Kutsyy et al. | |
| 2007/0250000 | A1* | 10/2007 | Magnin | A61B 8/4461 |
| | | | | 604/103.04 |
| 2008/0027695 | A1 | 1/2008 | Balgi et al. | |
| 2008/0201280 | A1 | 8/2008 | Martin et al. | |
| 2009/0112095 | A1* | 4/2009 | Daigle | A61B 8/06 |
| | | | | 600/454 |
| 2009/0171871 | A1 | 7/2009 | Zhang et al. | |
| 2009/0258925 | A1 | 10/2009 | Wahlestedt | |
| 2009/0259459 | A1 | 10/2009 | Ceusters et al. | |
| 2009/0284589 | A1* | 11/2009 | Radeva | G06T 7/0012 |
| | | | | 348/77 |
| 2009/0324126 | A1 | 12/2009 | Zitnick et al. | |
| 2010/0070448 | A1 | 3/2010 | Omoigui | |
| 2010/0262545 | A1 | 10/2010 | Herlitz | |
| 2010/0299135 | A1* | 11/2010 | Fritsch | G06F 40/30 |
| | | | | 704/9 |
| 2010/0312120 | A1* | 12/2010 | Meier | A61B 8/5223 |
| | | | | 600/459 |
| 2011/0026798 | A1 | 2/2011 | Madabhushi et al. | |
| 2011/0027181 | A1 | 2/2011 | Amodei et al. | |
| 2011/0218822 | A1* | 9/2011 | Buisman | G16H 15/00 |
| | | | | 705/3 |
| 2012/0035963 | A1 | 2/2012 | Qian et al. | |
| 2012/0147440 | A1* | 6/2012 | Shindo | H04N 1/33307 |
| | | | | 358/474 |
| 2012/0238888 | A1* | 9/2012 | Bredno | A61B 6/507 |
| | | | | 600/504 |
| 2012/0278060 | A1 | 11/2012 | Cancedda et al. | |
| 2013/0004044 | A1* | 1/2013 | Ross | G06T 7/136 |
| | | | | 382/131 |
| 2013/0275094 | A1 | 10/2013 | Ortoleva | |
| 2014/0016097 | A1* | 1/2014 | Leonardi | A61B 5/6821 |
| | | | | 351/209 |
| 2014/0126770 | A1 | 5/2014 | Odessky et al. | |
| 2014/0316758 | A1* | 10/2014 | Yagi | A61B 5/026 |
| | | | | 703/9 |
| 2014/0365239 | A1 | 12/2014 | Sadeghi | |
| 2015/0106123 | A1* | 4/2015 | Amarasingham | G16H 10/60 |
| | | | | 705/3 |
| 2015/0154275 | A1 | 6/2015 | Senart et al. | |
| 2015/0213225 | A1* | 7/2015 | Amarasingham | G06F 19/00 |
| | | | | 705/2 |
| 2015/0234921 | A1 | 8/2015 | Li | |
| 2015/0324527 | A1 | 11/2015 | Siegel et al. | |
| 2016/0203599 | A1 | 7/2016 | Gillies et al. | |
| 2016/0300350 | A1* | 10/2016 | Choi | G06N 7/005 |
| 2016/0314580 | A1 | 10/2016 | Lloyd et al. | |
| 2016/0326588 | A1 | 11/2016 | Beier | |
| 2016/0364630 | A1 | 12/2016 | Reicher et al. | |
| 2017/0000567 | A1* | 1/2017 | Kim | G16H 20/40 |
| 2017/0046839 | A1* | 2/2017 | Paik | G06K 9/00147 |
| 2017/0154156 | A1* | 6/2017 | Sevenster | G16H 15/00 |
| 2017/0251988 | A1* | 9/2017 | Weber | A61B 8/523 |
| 2017/0329929 | A1* | 11/2017 | Fishman | A61B 5/0013 |
| 2017/0330320 | A1* | 11/2017 | Lynch | A61B 5/055 |
| 2017/0358079 | A1 | 12/2017 | Gilles et al. | |
| 2018/0325598 | A1* | 11/2018 | Strongosky | A61B 34/10 |
| 2019/0088352 | A1* | 3/2019 | Nicolaas | G16H 30/20 |
| 2019/0142528 | A1* | 5/2019 | Vertikov | A61B 8/488 |
| | | | | 600/424 |
| 2019/0200951 | A1* | 7/2019 | Meier | A61B 8/0841 |
| 2019/0242896 | A1* | 8/2019 | Gessner | B33Y 40/00 |
| 2019/0254846 | A1* | 8/2019 | Gianotti | A61F 2/95 |
| 2020/0193599 | A1* | 6/2020 | Mansi | G16H 50/20 |
| 2020/0334811 | A1* | 10/2020 | Mansi | H04L 67/12 |

OTHER PUBLICATIONS

Ahmadi, A., et al., Association of Coronary Stenosis and Plaque Morphology With Fractional Flow Reserve and Outcomes. JAMA Cardiol, 2016. 1(3): p. 350-7.

Ahmadi, A., et al., Lesion-Specific and Vessel-Related Determinants of Fractional Flow Reserve Beyond Coronary Artery Stenosis. JACC Cardiovasc Imaging, 2018. 11(4): p. 521-530.

Albuquerque, L.C., et al., Intraplaque hemorrhage assessed by high-resolution magnetic resonance imaging and C-reactive protein in carotid atherosclerosis. Journal of Vascular Surgery. 46(6): p. 1130-1137, 2007.

Alimohammadi, M., et al., Development of a Patient-Specific Multi-Scale Model to Understand Atherosclerosis and Calcification Locations: Comparison with In vivo Data in an Aortic Dissection. Front Physiol, 2016. 7: p. 238.

Aoki, T., et al., Peripheral Lung Adenocarcinoma: Correlation of Thin-Section CT Findings with Histologic Prognostic Factors and Survival 1. Radiology, 2001. 220(3): p. 803-809.

Atkinson, A.J., et al., Biomarkers and surrogate endpoints: Preferred definitions and conceptual framework*. Clinical Pharmacology & Therapeutics, 2001. 69(3): p. 89-95.

Bittencourt, M.S., et al., Prognostic Value of Nonobstructive and Obstructive Coronary Artery Disease Detected by Coronary Computed Tomography Angiography to Identify Cardiovascular Events. Circulation: Cardiovascular Imaging, 2014. 7(2): p. 282-291.

Buckler, A., et al., A Novel Knowledge Representation Framework for the Statistical Validation of Quantitative Imaging Biomarkers. Journal of Digital Imaging, 2013. 26(4): p. 614-629.

Buckler, A.J., et al., Quantitative imaging biomarker ontology (QIBO) for knowledge representation of biomedical imaging biomarkers. Journal of digital imaging : the official journal of the Society for Computer Applications in Radiology, 2013. 26(4): p. 630-41.

Buckler, A.J., et al., Quantitative imaging test approval and biomarker qualification: interrelated but distinct activities. Radiology, 2011. 259(3): p. 875-84.

Buyse, M., et al., The validation of surrogate endpoints in meta-analyses of randomized experiments. Biostatistics, 2000. 1(1): p. 49-67.

Cai, J., et al., In vivo quantitative measurement of intact fibrous cap and lipid-rich necrotic core size in atherosclerotic carotid plaque: comparison of high-resolution, contrast-enhanced magnetic resonance imaging and histology. Circulation, 2005. 112(22): p. 3437-44.

Castellano et al. "Texture analysis of medical images," Clinical Radiology, Dec. 1, 2004 (Dec. 1, 2004) vol. 59.

Chan, T.F. and L.A. Vese, Active contours without edges. IEEE Trans Image Process, 2001. 10(2): p. 266-77.

Choi et al. "Multiscale image segmentation using wavelet-domain hidden Markov models" IEEE Trans Image Process, Sep. 1, 2001 (Sep. 1, 2001), vol. 10.

(56) References Cited

OTHER PUBLICATIONS

Coenen, A., et al., Diagnostic accuracy of a machine-learning approach to coronary computed tomographic angiography-based fractional flow reserve: result from the Machine consortium. Circulation: Cardiovascular Imaging, 2018. 11(6): p. e007217.

De Bono, B., et al., The Open Physiology workflow: modeling processes over physiology circuitboards of interoperable tissue units Front Physiol, 2015. 6: p. 24.

De Graaf, M., et al., Automatic quantification and characterization of coronary atherosclerosis with computed tomography coronary angiography: cross-correlation with intravascular ultrasound virtual histology. Int J Cardiovasc Imaging, 2013. 29(5): p. 1177-1190.

De Weert, T.T., et al., In Vivo Characterization and Quantification of Atherosclerotic Carotid Plaque Components With Multidetector Computed Tomography and Histopathological Correlation. Arterioscler Thromb Vasc Biol, 2006. 26(10): p. 2366-2372.

DeMarco, J.K. and J. Huston, Imaging of high-risk carotid artery plaques: current status and future directions. Neurosurgical Focus, 2014. 36(1): p. E1.

Diaz-Zamudio, M., et al., Automated Quantitative Plaque Burden from Coronary CT Angiography Noninvasively Predicts Hemodynamic Significance by using Fractional Flow Reserve in Intermediate Coronary Lesions. Radiology, 2015. 276(2): p. 408-15.

Dong, L., et al., Carotid Artery Atherosclerosis: Effect of Intensive Lipid Therapy on the Vasa Vasorum—Evaluation by Using Dynamic Contrast-enhanced MR Imaging. Radiology, 2011. 260(1): p. 224-231.

Filardi, V., Carotid artery stenosis near a bifurcation investigated by fluid dynamic analyses. The neuroradiology journal, 2013. 26(4): p. 439-453.

Fleming, T.R. and D.L. DeMets, Surrogate end points in clinical trials: are we being misled? Ann Intern Med, 1996. 125(7): p. 605-13.

Freimuth, R.R., et al., Life sciences domain analysis model. J Am Med Inform Assoc, 2012. 19(6): p. 1095-102.

Fujimoto, S., et al., A novel method for non-invasive plaque morphology analysis by coronary computed tomography angiography. Int J Cardiovasc Imaging, 2014. 30(7): p. 1373-1382.

Gaston A. Rodriguez-Granillo1, Patricia Carrascosa1, Nico Bruining3, and a.H.M.G.-G. RonWaksman4, Defining the non-vulnerable and vulnerable patients with computed tomography coronary angiography: evaluation of atherosclerotic plaque burden and composition. European Heart Journal—Cardiovascular Imaging, 2016. 2016(17): p. 481-491.

Gevaert, O., et al., Non-small cell lung cancer: identifying prognostic imaging biomarkers by leveraging public gene expression microarray data—methods and preliminary results. Radiology, 2012. 264(2): p. 387-396.

Ghazalpour, A., et al., Thematic review series: The pathogenesis of atherosclerosis. Toward a biological network for atherosclerosis. J Lipid Res, 2004. 45(10): p. 1793-805.

Gupta, A., et al., Carotid Plaque MRI and Stroke Risk A Systematic Review and Meta-analysis. Stroke, 2013. 44(11): p. 3071-3077.

Gupta, A., et al., Detection of Symptomatic Carotid Plaque Using Source Data from MR and CT Angiography: A Correlative Study. Cerebrovasc Dis, 2015. 39(3-4): p. 151-61.

Gupta, A., et al., Intraplaque high-intensity signal on 3D time-of-flight MR angiography is strongly associated with symptomatic carotid artery stenosis. American Journal of Neuroradiology, 2014. 35(3): p. 557-561.

Hecht, H.S., Coronary artery calcium scanning: past, present, and future. JACC Cardiovasc Imaging, 2015. 8: p. 579-596.

Hecht, H.S., J. Narula, and W.F. Fearon, Fractional Flow Reserve and Coronary Computed Tomographic Angiography A Review and Critical Analysis. Circ Res, 2016. 119(2): p. 300-16.

Helft, G., et al., Progression and regression of atherosclerotic lesions: monitoring with serial noninvasive magnetic resonance imaging. Circulation, 2002. 105(8): p. 993-8.

Inoue, K., et al., Serial Coronary CT Angiography-Verified Changes in Plaque Characteristics as an End Point: Evaluation of Effect of Statin Intervention. JACC: Cardiovascular Imaging, 2010. 3(7): p. 691-698.

International Search Report & Written Opinion in co-pending international patent application No. PCT/US16/67463 dated Mar. 10, 2017 (10 pages).

International Search Report & Written Opinion in co-pending international patent application No. PCT/US2016/065132 dated Mar. 17, 2017.

Khan et al. "Robust atlas-based brain segmentation using multi-structure confidence-weighted registration" Proceedings of the 12th International Conference on Medical Image Computing, Sep. 20, 2009.

Krizhevsky, A., I. Sutskever, and G.E. Hinton. Imagenet classification with deep convolutional neural networks. in Advances in neural information processing systems. 2012.

Lobatto, M.E., et al., Multimodal Clinical Imaging To Longitudinally Assess a Nanomedical Anti-Inflammatory Treatment in Experimental Atherosclerosis. Molecular Pharmaceutics, 2010. 7(6): p. 2020-2029.

Ma, X., et al., Volumes Learned: It Takes More Than Size to "Size Up" Pulmonary Lesions. Acad Radiol, 2016. 23(9): 1190-8.

Melander, O., et al., Novel and conventional biomarkers for prediction of incident cardiovascular events in the community. JAMA : the journal of the American Medical Association, 2009. 302(1): p. 49-57.

Miao, C., et al., The Association of Pericardial Fat with Coronary Artery Plaque Index at MR Imaging: The Multi-Ethnic Study of Atherosclerosis (MESA). Radiology, 2011. 261(1): p. 109-115.

Mono, M.L., et al., Plaque Characteristics of Asymptomatic Carotid Stenosis and Risk of Stroke. Cerebrovascular Diseases, 2012. 34(5-6): p. 343-350.

Narula, J., et al., Histopathologic characteristics of atherosclerotic coronary disease and implications of the findings for the invasive and noninvasive detection of vulnerable plaques. Journal of the American College of Cardiology, 2013. 61(10): p. 1041-1051.

Naylor, A.R., Identifying the high-risk carotid plaque. The Journal of Cardiovascular Surgery, 2014. 55(2): p. 11-20.

Perera, R. and P. Nand, Recent Advances in Natural Language Generation: A Survey and Classification of the Empirical Literature. vol. 36. 2017. 1-31.

Prentice, R.L., Surrogate endpoints in clinical trials: definition and operational criteria. Statistics in medicine, 1989. 8(4): p. 431-440.

Prescott, J., Quantitative Imaging Biomarkers: The Application of Advanced Image Processing and Analysis to Clinical and Preclinical Decision Making. Journal of Digital Imaging, 2013. 26(1): p. 97-108.

Reddy et al. "Confidence guided enhancing brain tumor segmentation in multi-parametric MRI" Proceedings of the 12th International Conference on Medical Image Computing and Computer-Assisted Intervention, MICCAI 2009, held in London, UK, Sep. 20, 2009.

Saba, L., et al., Carotid Artery Plaque Characterization Using CT Multienergy Imaging. American Journal of Neuroradiology, 2013. 34(4): p. 855-859.

Sadot, A., et al., Toward verified biological models. IEEE/ACM Trans Comput Biol Bioinform, 2008. 5(2): p. 223-34.

Sargent, D., et al., Validation of novel imaging methodologies for use as cancer clinical trial end-points. European Journal of Cancer, 2009. 45(2): p. 290-299.

Stary, H.C., et al., A definition of advanced types of atherosclerotic lesions and a histological classification of atherosclerosis A report from the Committee on Vascular Lesions of the Council on Arteriosclerosis, American Heart Association. Circulation, 1995. 92(5): p. 1355-1374.

Stary, H.C., Natural history and histological classification of atherosclerotic lesions: an update. Arterioscler Thromb Vasc Biol, 2000. 20(5): p. 1177-8.

Van 't Klooster, R., et al., Visualization of Local Changes in Vessel Wall Morphology and Plaque Progression in Serial Carotid Artery Magnetic Resonance Imaging. Stroke, 2014. 45(8): p. e160-e163.

Virmani, R., et al., Pathology of the Vulnerable Plaque. JACC, 2006. 47(8): p. C13-8.

(56) References Cited

OTHER PUBLICATIONS

Voros, S., et al., Coronary Atherosclerosis Imaging by Coronary CT Angiography. JACC Cardiovasc Imaging, 2011. 4(5): p. 537-48.
William B. Kerr et al. "A Methodology and Metric for Quantitative Analysis and Parameter Optimization of Unsupervised, Multi-Region Image Segmentation", Proceeding of the 8th IASTED International Conference on Signal and Image Processing, Aug. 14, 2006, pp. 243-248.
Zavodni, A.E.H., et al., Carotid Artery Plaque Morphology and Composition in Relation to Incident Cardiovascular Events: The Multi-Ethnic Study of Atherosclerosis (MESA). Radiology, 2014. 271(2): p. 381-389.
Ariff et al. "Carotid Artery Hemodynamics: Observing Patient-specific Changes with Amlodipine and Lisinopril by Using MRI Imaging Computation Fluid Dynamics." Radiol. 257.3(2010):662-669.
Bourque et al. "Usefulness of Cardiovascular Magnetic Resonance Imaging of the Superficial Femoral Artery for Screening Patients with Diabetes Mellitus for Artherosclerosis." Am. J. Cardiol. 110.1(2012):50-56.
Buckler et al. "A Collaborative Enterprise for Multi-Stakeholder Participation in the Advancement of Quantitative Imaging." Radiol. 258.3(2011):906-914.
Buckler et al. "Data Sets for the Qualification of CT as a Quantitative Imaging Biomarker in Lung Cancer." Optics Exp. 18.14(2010):16.
Buckler et al. "Data Sets for the Qualification of Volumetric CT as a Quantitative Imaging Biomarker in Lung Cancer." Optics Exp. 18.14(2010):15267-15282.
Buckler et al. "Standardization of Quantitative Imaging: The Time is Right and 18F-FDG PET/CT is a Good Place to Start." J. Nuclear Med. 52.2(2011):171-172.
Buckler et al. "The Use of Volumetric CT as an Imaging Biomarker in Lung Cancer." Acadmic Radiol. 17.1(2010):100-106.
Buckler et al. "Volumetric CT in Lung Cancer: An Example for the Qualification of Imaging as a Biomarker." Academic Radiol. 17.1(2010):107-115.
Freedman et al. "Statistical Validation of Intermediate Endpoints for Chronic Diseases." Stat. Med. 11(1992):167-178.
Fuleihan et al. "Reproducibility of DXA Absorptiometry: A Model for Bone Loss Estimates." J. Bone Miner. Res. 10.74(1995):1004-1014.
Horie et al. "Assessment of Carotid Plaque Stability Based on Dynamic Enhancement Pattern in Plaque Components with Multidetector CT Angiography." Stroke. 43.2(2012):393-398.
Irace et al. "Human Common Carotid Wall Shear Stress as a Function of Age and Gender: A 12-year Follow-up Study." AGE. 34.6(2012):1553-1562.
Jaffe, "Measures of Response: RECIST, WHO, and New Alternatives." J. Clin. Oncol. 24.20(2006):3245-3251.
Katz, "Biomarkers and Surrogate Markers: An FDA Perspective." NeuroRx. 1.2(2004):189-195.
Kerwin et al. "MRI of Carotid Artherosclerosis." Am. J. Roentgenol. 200.3(2013):W304-W313.
Kim et al. "A Curve Evolution-based variational approach to Simultaneous Image Restoration and Segmentation." EEE Int. Conf. Image Proc. (2002):1-109.
Lathia et al. "The Value, Qualification, and Regulatory Use of Surrogate End Points in Drug Development." Clin. Pharmacol. Therapeutics. 86.1(2009):32-43.
Mozley et al. "Change in Lung Tumor Volume as a Biomarker of Treatment Response: A Critical Review of the Evidence." Ann. Oncol. 21.9(2010):1751-1755.
Phinikaridou et al. "Regions of Low Endothelial Shear Stress Colocalize with Positive Vascular Remodeling and Atherosclerotic Plaque Disruption: An in vivo Magnetic Resonance Imaging Study." Circ. Cardiovasc. Imaging. 6.2(2013):302-310.
Sui et al. "Assessment of Wall Shear Stress in the Common Carotid Artery of Healthy Subjects Using 3.0-Tesla Magentic Resonanance." Acta Radiologica. 49.4(2008):442-449.
Ten Kate et al. "Noninvasive Imaging of the Vulnerable Atherosclerotic Plaque." Current Problems Cardiol. 35.11(2010):556-591.
Van Klavern et al. "Management of Lung Nodules Detected by Volume CT Scanning." New Engl. J. Med. 361(2009):23.
Varma et al. "Coronary Vessel Wall Constrast Enhancement Imaging as a Potential Direct Marker of Coronary Involvement: Integration of Findings from CAD and SLE Patients." JACC Cardiovasc. Imaging. 7.8(2014):762-770.
Wintermark et al. "Carotid Plaque CT Imaging in Stroke and Non-Stroke Patients." Ann. Neurol. 64.2(2008):149-157.
Wintermark et al. "High-Resolution CT Imaging of Carotid Artery Atherosclerotic Plaques." Am. J. Neuroradiol. 29.5(2008):875-882.
Wong et al. "Imaging in Drug Discovery, Preclinical, and Early Clinical Development." J. Nuclear Med. 49.6(2008):26N-28N.
Woodcock et al. "The FDA Critical Path Initiative and its Influence on New Drug Development." Annu. Rev. Med. 59(2008):1-12.
Zhao et al. "Evaluating Variability in Tumor Measurements from Same-Day Repeat CT Scans of Patients with Non-Small Cell Lung Cancer." Radiol. 252.1(2009):263-272.
European Search Report for Appl. No. 18845291.6 dated Apr. 26, 2021.

* cited by examiner

FIG. 8 vascuCAP

Work Item Provenance

- 2017-04-19T15:09:48-04;
  Step: workItem::specific
  By: Xiaonan Ma
- 2017-04-19T15:09:46-04;
  Step: workItem::specific
  By: Xiaonan Ma
- 2017-04-19T11:06:39-04;
  Step: workItem::specific
  By: Xiaonan Ma
- 2017-04-18T11:27:55-04;
  Step: targetDefine::Com
  By: Xiaonan Ma
- 2017-04-18T11:27:48-04;
  Step: patientAnalyze::m
  By: Xiaonan Ma
- 2017-04-18T11:27:34-04;
  Step: targetDefine::Com
  By: Xiaonan Ma
- 2017-04-18T11:27:16-04;
  Step: targetDefine::Com
  By: Xiaonan Ma Elucid Bioimaging Back to Analyze

---

Hi Samantha! | Admin | Sign out vascuCAP — ...oring for Vasculopathy (FDA)

[Export Button] [Export] [Target View ○ Lesion View] (Target View/Lesion View Toggle)

Sept. 23, 2011 | Jan. 11, 2012 | May 5, 2015 | Trends

MRN000000    (Patient ID)    Doe, John

Date of Birth: Nov. 1, 1929    (Demographics)
Age at Encounter: 85yrs, 6mths
Report Performer: Samantha St. Pierre
Creation Date: June 9, 2017    (Report Version)

Targets Defined: (Target Navigations)
- RightCarotid (RightCarotid)
  - left00
- LeftCarotid (LeftCarotid)
- RightCarotid (RightCarotid) (hide)

Structure (Structure Readings)

| Structure | ref | |
|---|---|---|
| Length | 67 mm | |
| MaxMaxWallThickness | 5.31 mm | |
| MaxRemodelingRatio | 2.62 (unitless ratio) | |
| MaxStenosisByArea | 94 % | |
| MaxStenosisByDiameter | 80 % | |
| MaxWallArea | 87 mm² | |
| MaxWallThickness | 5.39 mm | |
| PlaqueBurdenVolRatio | 0.51 (unitless ratio) | |

Composition (Tissue Characteristics)

| | | |
|---|---|---|
| CALCVol | 122 mm³ | |
| CALCVolProp | 0.04 (proportion of wall) | |
| LRNCVol | 634 mm³ | |
| LRNCVolProp | 0.23 (proportion of wall) | |
| MaxCALCArea | 16 mm² | |
| MaxCALCAreaProp | 0.19 (proportion of wall) | |
| MaxRNCArea | 24 mm² | |
| MaxRNCAreaProp | 0.47 (proportion of wall) | |

InternalCarotid  
MaxWT —  
MaxStenosis —  
MaxCALC —  
MaxMATC —

-- CommonCarotidArtery
— InternalCarotidArtery
--- LRNCArea
— CALCArea
--- MATxArea (Reading Key)

CAP Reading Key

CALCArea: Cross-sectional calcified area.

CALCAreaProp: Cross-sectional calcified area as a proportion of that cross-section's wall area.

CALCVol: Calcified volume, where calcification is thought to be the physiologic defensive process of attempting to stabilize plaque, which has a mechanism akin to bone formation. It is an accumulation of calcium salts in vascular tissue.

CALCVolProp: Calcified volume as a proportion of total wall volume.

LRNCArea: Cross-sectional LRNC area.

(Key Image)

Identity used for provenance: Samantha St. Pierre/Elucid Bioimaging (logged in to CAPgraph, press to logout)

FIG. 9

FIG. 10 vascuCAP   ☐ Computer-Aided Phenotyping for Vasculopathy (FDA)

MRN080800 (!) ☒ | Work Item List

Work Item Provenance 2017-04-19T15:09:48-04:
Step: workItem::specific
By: Xiaonan Ma 2017-04-19T15:09:46-04:
Step: workItem::specific
By: Xiaonan Ma 2017-04-19T11:06:38-04:
Step: workItem::specific
By: Xiaonan Ma 2017-04-18T11:27:55-04:
Step: targetDefine::Com
By: Xiaonan Ma 2017-04-18T11:27:54-04:
Step: targetDefine::Com
By: Xiaonan Ma 2017-04-18T11:27:51-04:

RightCarotid (RightCarotide) CommonCarotidArtery (show)

RightCarotid (RightCarotid) InternalCarotidArtery (hide)     *Vessel Context (with show/hide switch)*

| Structure | | Composition | |
|---|---|---|---|
| Length | 51 mm | CALCVol | 57 mm³ |
| LumenAndWallVol | 1455 mm³ | CALCVolProp | 0.07 (proportion of wall) |
| LumenVol | 611 mm³ | LRNCVol | 13 mm³ |
| MaxDilationByArea | 107 % | LRNCVolProp | 0.01 (proportion of wall) |
| MaxDilationByDiameter | 63 % | MATXVol | 721 mm³ |
| MaxLumenAndWallArea | 110 mm² | MATXVolProp | 0.85 (proportion of wall) |
| MaxLumenAndWallRatio | 2.38 (unitless) | MaxCALCArea | 10 mm² |
| MaxLumenArea | 39 mm² | MaxCALCAreaProp | 0.17 (proportion of wall) |
| MaxMaxWallThickness | 4.55 mm | MaxLRNCArea | 2.98 mm² |
| MaxRemodelingRatio | 2.38 (unitless) | MaxLRNCAreaProp | 0.07 (proportion of wall) |
| MaxStenosisByArea | 38 % | MaxMATXArea | 64 mm² |
| MaxStenosisByDiameter | 29 % | MaxMATXAreaProp | 0.97 (proportion of wall) |
| MaxWallArea | 73 mm² | | |
| MaxWallThickness | 4.57 mm | | |
| MinLumenArea | 11 mm² | | |
| PlaqueBurdenVolRatio | 0.58 (unitless ratio) | | |
| WallToLumenVolRatio | 1.38 (unitless ratio) | | |
| WallVol | 844 mm³ | | |

Comment: RightCarotid_RightCarotid_InternalCarotidArtery     *Vessel-level comment*

CAP Reading Key

CALCArea: Cross-sectional calcified area.

CALCAreaProp: Cross-sectional calcified area as a proportion of that cross-section's wall area.

CALCVol: Calcified volume, where calcification is thought to be the physiologic defensive process of attempting to stabilize Elucid Bioimaging ◁ Back to Analyze Identity used for provenance: Samantha St. Pierre/Elucid Bioimaging (logged in to CAPgraph, press to logout)

FIG. 13

| RightCarotid (RightCaro | 95% CI: 42.737 [42.373, 45.566] | | |
|---|---|---|---|
| Structure | CC(...) by Xiaonan Ma on 2017-04-18 | | |
| | CWT(...) by Xiaonan Ma on 2017-04-18 | | |
| LumenAndWallArea | CLAWP(...) by Xiaonan Ma on 2017-04-18 | | |
| | CLAWS(...) by Xiaonan Ma on 2017-04-18 | | |
| LumenArea | CR(...) by Xiaonan Ma on 2017-04-18 | | |
| MaxWallThickness | CLP(...) by Xiaonan Ma on 2017-04-18 | | |
| | CVTP(...) by Xiaonan Ma on 2017-04-18 | | |
| PlaqueBurdenAreaRatio | CLS(...) by Xiaonan Ma on 2017-04-18 | | |
| RemodelingRatio | initializer from 1.3.6.1.4.1.5962.99.1.3201072250.1814720371.1463489985658.477.0(...) by Xiaonan Ma on 2017-04-18 | | |
| StenosisByArea | initializer from 1.3.6.1.4.1.5962.99.1.3201072250.1814720371.1463489985658.477.0(...) by Xiaonan Ma on 2017-04-18 | | |
| WallArea | 43 mm² | MATXArea | |
| | | MATXAreaProp | 0.69 |

FIG. 14

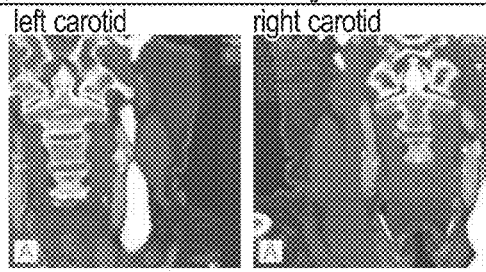

MRN000000   Doe, John   May 5, 2015

Date of Birth: None
Age at Encounter:
Report Performer: Larry Martell
Creation Date: Aug. 4, 2017

Indication
Carotid Artery Stenosis (CAS)
Procedure
acquisitionDatetime: 2015-05-05 10:46:06
mAs/sliceThickness/kVp: 271, 0.75, 120
make/model: SIEMENS SOMATOM Definition AS
modality/contrastAgent/anatomy: CT, APPLIED, HEAD left carotid    right carotid

Findings
The right carotid presents with 36.4mm long atheromatous plaque centered 6.0mm from the origin of the ICA. The calcified atheromatous plaque has severe remodeling and a large lipid core. The lesion is likely type VI however could be type V.
The right carotid presents with 1.5mm long atheromatous plaque centered 14.4mm from the origin of the ICA. The atheromatous plaque has remodeling and a lipid core. The lesion is likely type V or type VI.
The left carotid presents with 2.5mm long atheromatous plaque centered 9.9mm distal from the origin. The calcified atheromatous plaque has severe wall thickening and a lipid core. The lesion is likely type V or type VI.
The left carotid presents with 27.0mm long atheromatous plaque centered 2.8mm from the origin of the ICA. The highly dilated, highly calcified atheromatous plaque has severe remodeling and a large lipid core. The lesion is likely type V or type VI.

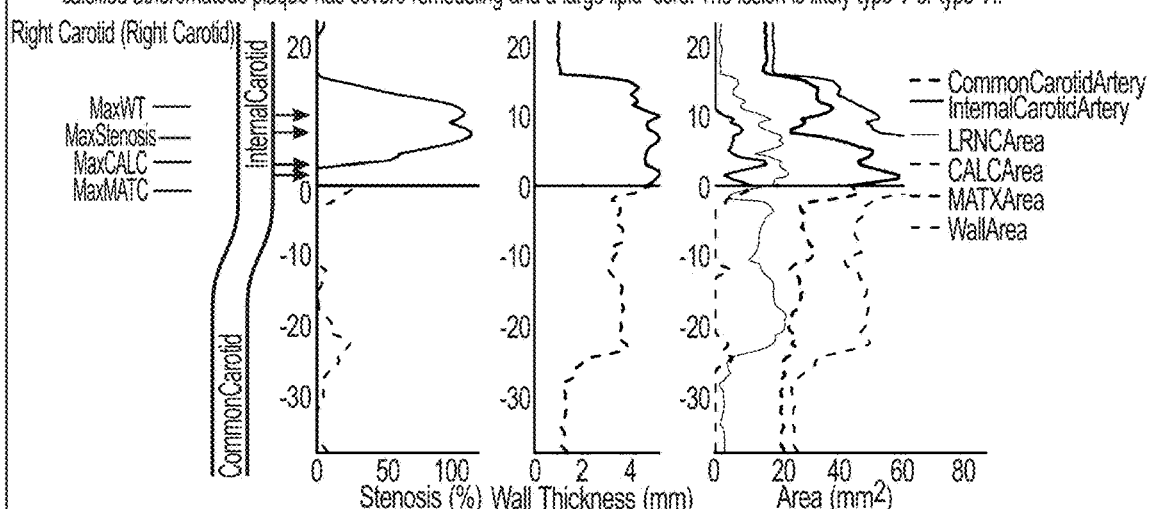

RightCarotid (RightCarotid) InternalCarotidArtery 1.5 mm (MaxLRNC) (MaxMATX)

| Structure | | Composition | |
|---|---|---|---|
| lumenAndWallArea | 116 mm2 | CALCArea | 2.76 mm2 |
| LumenArea | 29 mm2 | CALCAreaProp | 0.03 |
| MaxWallThickness | 5.26 mm | LRNCArea | 24 mm2 |
| PlaqueBurdenAreaRatio | 0.75 | LRNCAreaProp | 0.27 |
| RemodelingRatio | 2.62 | MATXArea | 59 mm2 |
| StenosisByArea | 0.00 % | MATXAreaProp | 0.68 |
| WallArea | 87 mm2 | | |

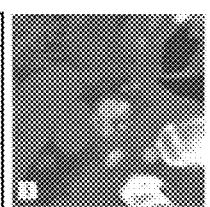

Impression
These findings confer a 88% likelihood of the patient experiencing an ischemic stroke or TIA according to the Stroke model, an increase of 45% relative to 2012-01-11 11:26:28.
These findings confer a 57% likelihood of the patient experiencing an ischemic stroke or TIA according to the Book model, a decrease of 33% relative to 2012-01-11 11:26:28.
These findings confer a 22% likelihood of the patient experiencing an ischemic stroke or TIA according to the Neuro model, a decrease of 36% relative to 2012-01-11 11:26:28.

FIG. 15

Elucid Bioimaging

Computer-Aided Phenotyping for Vasculopathy - INVESTIGATIONAL DEVICE NOT

TASKS
Patients

Patients

| Patient ID | | Patient Res | | Name | | DOB | | Sex | |

[Regenerate Patient List] [Delete]

<<< Displaying 1 to 10 of 10 >>>

| Delete | Patient ID | Patient Res | First Name | Last Name | DOB | Sex |
|---|---|---|---|---|---|---|
| ☐ | 88379731 | 2107659134488650843 | Q-CAMP-02-0018 | | 1952-02-16 | M |
| ☐ | 33874675 | 6932137026717543136 | | | 1929-11-22 | F |
| ☐ | 91840742 | 2753300867266938451 | | | 1940-02-11 | M |
| ☐ | 15826591 | 5842735662145585211 | | | 1947-09-15 | M |
| ☐ | 71489528 | 8242525593783618182 | | | 1937-01-09 | M |
| ☐ | EMPTY | 1238450914716167607 | dpe | john | | |
| ☐ | 4. report | 6896759490489614636 | 02-0014 | | | |
| ☐ | NECK-155 | 9401402058704395286 | NECK-155 | | | F |
| ☐ | anterior circulation | 9108546338981586787 | intracranial | | | F |
| ☐ | MRN000000 | 7624128244628810951 | John | Doe | 1929-11-01 | M |

Terms
End-user Licence
Acceptable Use
Privacy and Data Lifetime
Report a bug

Norton SECURED
powered by Symantec
ABOUT SSL CERTIFICATES

QUANTITATIVE MEDICAL IMAGING REPORTING

RELATED APPLICATIONS

This application claims priority to and benefit of U.S. provisional application No. 62/544,298, filed Aug. 11, 2017, incorporated by reference herein in its entirety for all intents and purposes.

The subject application relates to PCT/US16/65132, filed Dec. 6, 2016 and entitled: SYSTEMS AND METHODS FOR ANALYZING PATHOLOGIES UTILIZING QUANTITATIVE IMAGING and PCT/US16/67463, filed Dec. 19, 2016 and Entitled: METHODS AND SYSTEMS FOR REPRESENTING, STORING, AND ACCESSING COMPUTABLE MEDICAL IMAGING-DERIVED QUANTITIES, the contents of both of which are hereby incorporated herein in their entireties.

STATEMENT REGARDING FEDERALLY SPONSORED RESEARCH OR DEVELOPMENT

This disclosure was supported in part by the U.S. Government under NIH Grant R44HL126224, NIH Grant KL2TR000458, and NSF Grant 1353532. The Government has certain rights in the invention.

BACKGROUND

Cardiovascular diseases (CVD) encompasses stroke, peripheral artery disease, and coronary heart disease. It is the most common cause of death in the developed world, with someone dying from it every 34 seconds in the U.S. Nearly half (47%) of all deaths are from CVD. Although the death rate from cardiovascular disease continues to fall in the developed world, the number of hospitalizations and long-term disabilities is increasing. However, in developing nations such as China and India, there is an increasing incidence of CVD due in part to the Westernization of their diet and epigenetic effects on their gene expression patterns. Early assessment of atherosclerotic plaques prior to thromboembolic events, such as myocardial infarction or ischemic stroke, is an important diagnostic priority for at-risk patients. Computed tomography angiography (CTA) is a useful diagnostic test in the emergency room and is associated with shorter stays and time to diagnosis.

Completed clinical trials have shown significant benefits of carotid surgeries for symptomatic patients with severe carotid artery stenosis (CAS). However, evidence increasingly suggests that significant arterial stenosis alone is a sub-optimal marker for identifying patients at risk. In the European Carotid Surgery Trial (ECST), 30% of the 440 symptomatic patients who did not undergo surgery with a stenosis of <50% reported stroke or death on follow-up. Ultrasound is an accessible modality that provides a useful first examination, with its limitations to quantitatively measure tissue composition being augmented with CTA and magnetic resonance (MR). If bilateral carotid artery disease is detected, patients may be referred for coronary artery imaging since this occurrence has been linked to coronary events to determine if they are candidates for intensive medical therapy or, for those with carotid stenosis >70%, carotid endarterectomy or stenting. If less severe disease is detected, the patient will be treated with tailored medical therapy and could be reevaluated periodically by imaging, and in a few centers by PET imaging to assess the inflammatory status.

Solutions are critical to preempt events or at least improve diagnostic accuracy on presentation. Accurate elucidation of phenotype enables prompt intervention. There is growing evidence that non-invasive CTA and MR have the potential to examine components that have been demonstrated to contribute to atherosclerosis. For example, expansive arterial remodeling was strongly associated with symptomatic plaques in initial studies performed on post-mortem coronary arteries and later confirmed in the carotid arteries. Similarly, lipid-rich necrotic core is shown to be a predictor of incident stroke when detected non-invasively. Calcification, which manifests in current clinical assessment of coronary arteries, is an established marker of atherosclerosis and predictor of coronary events, myocardial infarction, and death. However, simplistic measures such as the calcium score fail to provide a granular assessment that accounts for the more nuanced role that calcium plays depending on its presentation.

In addition to the large number of patients with acute atherosclerosis, up to 30 million U.S. patients are currently on statin therapy in an attempt to avoid CVD. Yet efforts to develop new therapeutic options to slow or stop the disease are limited to using serum cholesterol, a non-specific biomarker, or to wait for events. It is difficult for new therapies like CETP and PCSK-9 inhibitors to demonstrate efficacy in a commercially reasonable timeframe. A sample size of 27,000 patients in the FOURIER study of Repatha (evolocumab) failed to show survival benefits despite significantly reducing adverse events. This could be overcome with measurement of the patients' extent of plaque and plaque phenotyping as a cost-effective companion diagnostic for more expensive, newer drugs. Moreover, drug candidates in other therapeutic areas, such as immuno-modulators in cancer, can have side effects where atherosclerosis is aggravated, but accurate methods are needed to assay these effects. Whether for clinical care of individual patients, or clinical research on cohorts, these studies emphasize the desire for biomarkers beyond population-based clinical variables with an interest in personalizing the patient condition. Consequently, the complexity of interpreting these biomarkers in potentially multi-dimensional datasets may create inefficiencies in the clinical workflow. The data must be presented in a standardized manner to offer both clarity and completeness of the analysis and present new actionable medical information to improve clinical management decision-making.

Medical imaging, such as computed tomography (CT) and MR, has been ranked by physicians as the single most important medical innovation. The rich information in imaging extends far beyond the numerical values of the pixels—it involves describing imaging biomarkers that are indicators of the underlying biology of interest. From its inception, imaging has allowed visualization of the in vivo characteristics of disease. Structural measurements of anatomic structure have long been and remain the single most used measurements in patient care. Quantitative assessment of constituent tissue components or characteristics, molecular mechanisms, and hemodynamic parameters may provide additional information about the pathogenesis and natural history of disease.

Increasingly, incisive clinical insights are possible and image analysis methods are continuously developed to implement them, yet the increasing capability requires ever more sophisticated computational techniques to exploit. Quantitative imaging techniques are developed for use in the clinical care of patients and in the conduct of clinical trials. The biological significance of these imaging studies often involves identifying imaging biomarkers that are indicators of the underlying biology. Quantitative imaging biomarkers provide a numerical characterization of the underlying biology or pathology as opposed to using textual or categorical descriptions of an observer's subjective visual interpretation. In clinical practice, quantitative imaging may be used to detect and characterize disease before, during, and after a course of therapy, and used to predict the course of disease. In clinical research, quantitative imaging biomarkers are used to define endpoints of clinical trials. Tools have become available for handling the complexity of genotype, and similar advancements are needed to handle the complexity of phenotype, especially as derived from imaging. However, information resources for in vivo biomarkers, specifically quantitative imaging biomarkers, are notably lacking. Quantitative imaging suffers from the lack of a standardized representation of quantitative image features and content, and manually interpreting multi-dimensional datasets may create inefficiencies in the clinical work flow.

Most current radiology reports are unstructured subjective clinical narratives that are qualitative in nature. This is largely driven by tradition and the ease of dictating notes with a sophisticated speech recognition system. As a result, it is unclear to radiologists how to best integrate information that is inherently quantitative and objective into these reports. There have been many attempts in structuring radiology reports for consistency, accuracy, and minable data, such as eDictation, StructuRad, and PointDx, but none have quite reached widespread adoption. In fact, one study comparing a form of structured reporting against dictation reporting resulted in higher accuracy, completeness, and satisfaction in the latter among radiology residents, even though the users were optimistic to the appeal of structured reporting. However, radiologists are generally adverse to adopting systems that may introduce inefficiencies in their workflows. Despite significant support for standardization of radiology reports, the transition is decidedly slow and there is an inherent "chicken and egg" problem: radiologists cannot implement innovative reporting methods because the technology does not exist, and the technology does not exist because it is not sought by radiologists. Nevertheless, there is a consensus among radiology leadership that structured reporting is desired and that a hybrid approach of speech recognition and structured data elements has merit.

The introduction of new quantitative biomarkers faces similar issues as structured reporting systems. The data should be presented in a way that does not impede on efficiency of the clinical workflow and must provide new interpretable information to help clinicians make better patient management decisions, otherwise what is supposed to be an advantage instead becomes a burden. As a counter-example, presenting lengthy tables of intricate quantitative data for every measurement at every anatomical location is not digestible by a human and fails to bring a desired focus to the most significant measurements or insights drawn from them. A summary statement based in quantitative data but expressed in natural language to represent the data may be needed to ease the communication of new relevant medical knowledge to clinical management decision makers, with capability to drill down or refer to more detailed measurement data to whatever level the clinician desires, rather than assuming that they want the whole.

To meet the first need, a form of natural language processing (NLP) is needed to generate a clinically actionable statement in a report. Before 2010, the development of biomedical text mining with natural language processing (NLP) was driven by the increase of publication rate indicated by the growth of content in PubMed/MEDLINE. The increase in use of high-throughput assays, for example, to produce lists of genes increased the rate of discovery of new biological entities but consequently was overwhelming without the means to make the information digestible. The NLP applications in biomedical research made a corresponding case for using NLP in proactive clinical decision support (CDS) systems. In the context of radiology reports, several systems, such as the Special Purpose Radiology Understanding System (SPRUS), the Natural Language Understanding Systems (NLUS), Symbolic Text Processor (SymText), and MPLUS (M+), extract radiologist interpretations and code findings in hopes of providing relevant clinical data to an expert CDS system.

While these NLP applications are primarily used to convert clinical narrative text to concise computer-interpretable data elements, no application has been used to generate medical narrative text from quantitative imaging data. Natural language generation (NLG) is the natural language processing task of generating natural language from a machine representation system such as a knowledge base or a logical form. In other fields, NLG systems have been used to convert or translate structured data into a natural language representation. The used methods to produce the final language are different from those of a compiler due to the inherent expressivity of natural languages. NLG may be viewed as the opposite of NLP: whereas in NLP the system needs to disambiguate input texts to produce machine representations, in NLG the system needs to make decisions about how to put machine representations into output text.

Interpretation of data used in the development, validation, and use of quantitative imaging biomarkers requires many disparate concepts to be related together with scientifically rigorous epistemology. Ontologies form an ideal framework for the integration of heterogeneous and complex knowledge about imaging. Ontology-based annotation of datasets coupled with image archives capable of batch selection and processing, quantitative imaging biomarkers will experience increases in capability and adoption analogous to genetic biomarkers in molecular biology. By formally defining concepts and synonyms of concepts in the imaging domain, the use of ontologies helps eliminate variation and ambiguity in terminology, and thus can be used to link data and knowledge from different sources. Likewise, organized lexicons such as RadLex relate radiologist interpretations with other sources of medical concepts. By themselves, these lexicons only structure data abstractions, but when integrated into a processing system, they can aid in the representation and structuring of output produced by a system. Reporting based on ontology to represent the complex and heterogeneous imaging biomarker data and knowledge would enable not just the exposition of data, but the computer aided drawing of insights from that data.

SUMMARY

Disclosed herein are advanced reporting systems based in part on ontology development for quantitative imaging biomarkers, information modeling to integrate heterogeneous data types relevant to quantitative medical analysis, and a knowledge representation framework for their statistical validation. The disclosure provides a meaningful and concrete method to realize the value of quantitative imaging in such a way as to enhance rather than degrade clinical workflow productivity, featuring: 1) a reporting engine integrated with quantitative imaging application software that integrates reporting logic to a rich data representation based on ontology; 2) an in-built knowledge graph that persists data for clinical decision support and discovery research; 3) an expressive natural language interpretation of underlying objective and quantitative measurement data; 4) drill down capability highlighting the specific pathology tied to findings; and 5) a hierarchically organized detailed chart with varying levels of summarization reaching down to a level which would otherwise only be available ex vivo but which, by the methods of this disclosure, is accessible non-invasively in vivo. Analysis of vasculopathy, such as atherosclerosis and vasculitis, is used as a case study of these methods to evaluate its results within a tangible application targeted to CVD.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIG. 8 is a screen shot of the top of the vertical scrolling area of the report generator in Chart view;

FIG. 9 is a screen shot of analysis target or lesion-level summary;

FIG. 10 is a screen shot of vessel or segment level summary (hierarchically organized under target or lesion);

FIG. 13 is a screen shot of a pop-up screen available when right-clicking on any measured quantity;

FIG. 14 is a screen shot of a narrative view with two drill downs selected; and

FIG. 15 is a screen shot of the directory-style access via browser.

DETAILED DESCRIPTION

Figure 1:
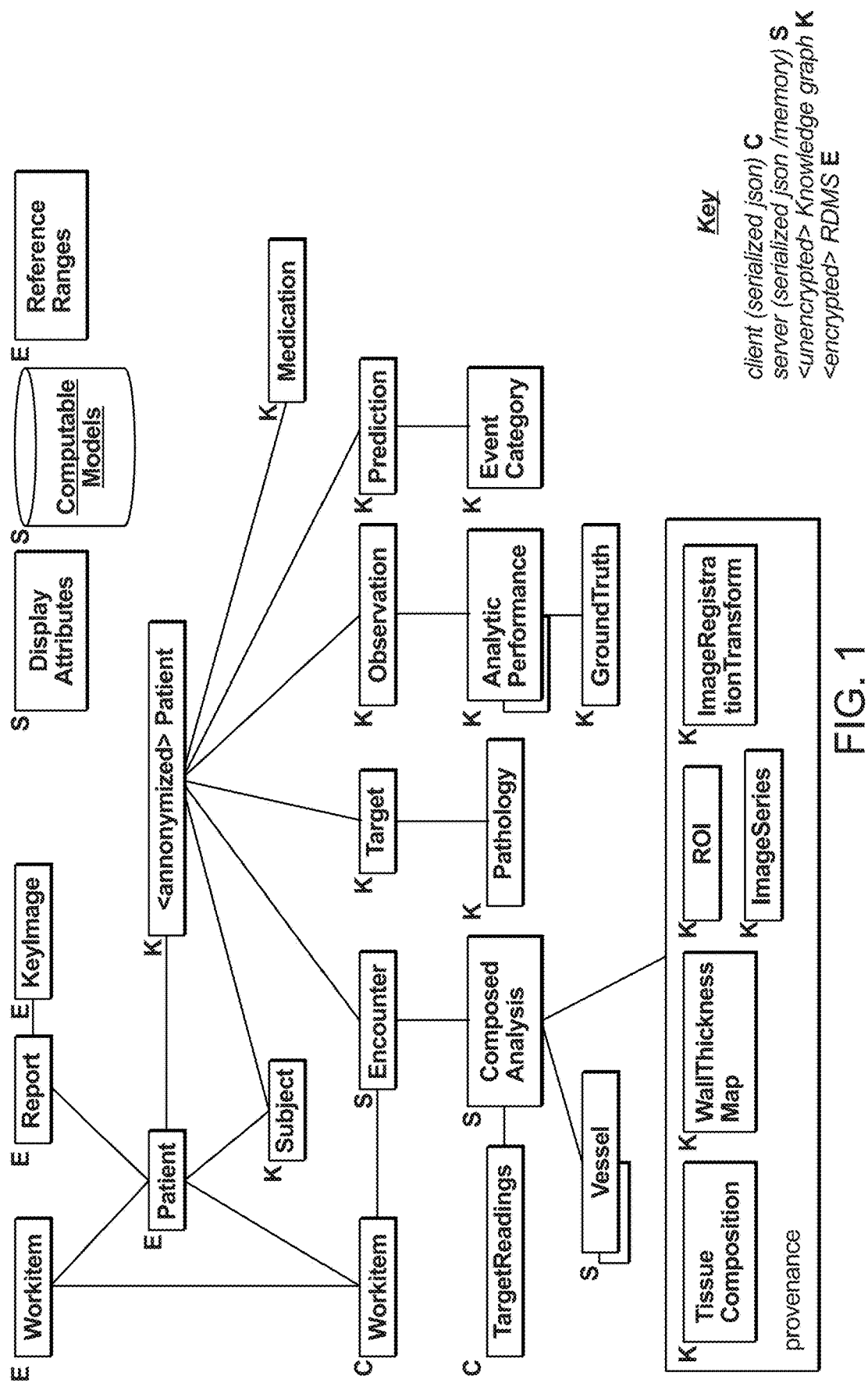
FIG. 1 is a diagram of an overview of classes.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

In example embodiments, systems and methods of the present disclosure may implement a report generation module including a natural language generator. The report generation module may be configured to receive a data set including quantitative and objective measurements of one or more biological properties of a patient. The report generation module may then advantageously process the data set using the natural language generator to automatically provide a natural language narrative including an objectively structured set of a plurality of findings based on the quantitative and objective measurements. Using this natural language narrative, the reporting module may then generate and display a report for the patient (i.e., where the report includes the natural language narrative).

In some embodiments, the generated report may be configured to correlate each of the plurality of findings in the natural language narrative with a specific quantitative data subset supporting that finding. Thus, in example embodiments, a user may advantageously use a user interface to selectively view the specific quantitative data subset correlated with each of the findings in the natural language narrative.

In example embodiments, the received data set may include a hierarchical data structure including one or more qualitative pathological features which are determined based (at least in part) on the quantitative and objective measurements of the one or more biological properties. These objective measurements of one or more biological properties (i.e. biomarkers) may further be determined based (at least in part) on image features extracted from imaging data (e.g., CT/MRI imaging data). Advantageously, the determined one or more qualitative pathological features may be indicative of therapeutic/treatment options or further diagnostics. The determined one or more qualitative pathological features may also be used in determining one or more predictive outcomes for the patient (which may further be informed based on contextual information such as patient demographics). Thus, in example embodiments, the hierarchical data structure may further include one or more predictive outcomes for a pathology.

In example embodiments, the natural language narrative may include an objective natural language interpretation of both the quantitative and objective measurements and the qualitative pathological features. Thus, e.g., wherein the qualitative pathological features may include phenotype classification for a pathology. In embodiments where the hierarchical data structure further includes one or more predictive outcomes for a pathology, the natural language narrative may also include an objective natural language interpretation of the one or more predictive outcomes for the pathology.

In some embodiments, machine learning may be utilized to train a first algorithm for identifying and quantifying (objectively) the measurements of the one or more biological properties based (at least in part) on imaging data. Machine learning may also be utilized to train a second algorithm for identifying and qualifying the pathological features based (at least in part) on the quantified measurements of the one or more biological properties. Advantageously, the first and second machine learned algorithms may be independently derived (i.e., distinctly trained).

In some embodiments, a training set from one or more non-radiological or non-imaging data sources may be used in training an algorithm for identifying and quantifying (objectively) the measurements of the one or more biological properties based (at least in part) on radiological imaging data. Non-imaging sources may include, e.g., one or more of (i) demographics, (ii) results from cultures or other lab tests, (iii) genomic, proteomic or metabolomic expression profiles, or (iv) diagnostic observations.

In further example embodiments, systems and methods of the present disclosure may implement a report generation module configured to receive a data set including quantitative and objective measurements of one or more biological properties of a patient (e.g., from imaging data) and use an ontological data model including a taxonomic hierarchy of biomedical concepts related to a domain of biological properties to (e.g., wherein the ontological data model includes semantic relationships between biomedical concepts) to analyze the data set and generate and display a report for the patient based on ontology from the ontological data model. Advantageously, the report may utilize pre-computed data points and information from older data sets to reduce processing time. In some embodiments the report may include longitudinal trend analysis based on ontology from the ontological data model. Longitudinal trend analysis may similarly include using pre-computed data points and information for a trend from older data sets to reduce processing time. In example embodiments, the taxonomic hierarchy of biomedical concepts may include a hierarchical characterization of a target anatomical site. For example, the hierarchical characterization of the target anatomical site may include characterization of a vessel, a vessel segment, and a segment cross-section as well as a characterization of an anatomic region for the vessel.

In some embodiments, the ontological data model may include/define relationships between qualitative pathological features and quantitative the report may advantageously be configured to include one or more qualitative pathological features for the patient which are automatically and objectively determined based on the ontological data model.

The one or more qualitative pathological features may include phenotype classification for a pathology and may provide for computer aided detection of a pathology.

In example embodiments, the systems and methods of the present disclosure may advantageously employ a client server architecture. Thus, in some embodiments, a server may be configured to receive a request from a client whereby such request triggers the generation of a report. In such embodiments, the server may be advantageously configured to work ahead and pre-compute available report information prior to receiving a client request to reduce processing time.

Referring now to the preferred embodiments in the figures, the systems and methods of the present disclosure may typically involve multiple components, including a data model covering the key concepts necessary to capture quantitative imaging results tied to objectively verifiable biophysical concepts. This data model may be implemented utilizing a RDBMS integrated with a knowledge graph for linked data supporting inference over large, sparse, data sets. Express consideration for HIPAA requirements is in the design, while still allowing access to data for clinical care and clinical research use cases. The reporting system logic and user interfaces may be architected with a client-server infrastructure capable of efficient operation and implemented in the best of contemporary frameworks. Specific logic supporting application methods may use these components to meet specific use cases.

A "Chart" view may be organized hierarchically by anatomic site and as a result offer a comprehensive view as needed, whereas A "Narrative" may draw inspiration directly from the radiology reports that clinicians are used to seeing, but incorporate the unique capabilities of the CAP platform to increase the value of radiology without forcing an overwhelming presentation which could compromise that value in practice. The basic principles of the Narrative view are to use plain language as well as accepted words (e.g., qualifiers) like "normal" and "severe" rather than cryptic acronyms and numbers, but do so without losing the value of the quantitative and objection analysis numbers (which may be advantageously made accessible using a drill down architecture). Drill downs may be advantageously accessible via a user interface (e.g., by single clicks, hovering, highlighting, etc.) to go directly to a detected pathology which may be augmented by the Chart view (provided to allow as high a level of detail as may be needed, for example, for procedure planning beyond more simplified diagnostic use cases). Thus, the Narrative view may focus on the subset of the quantitative analysis found to be abnormal, while the Chart may advantageously place normal or abnormal measurements in context (e.g., relative to one another or relative to a patient population or demographics).

The initial system-generated text in the Narrative view may be presented so as to be fully editable by the clinician, enabling full control to change the way a sentence is worded if they do not like it, or delete it altogether. Definitions of "normal", "severe" or other classifiers may advantageously draw from a table of value ranges initialized from batch processing of reference case data. In some embodiments, the table of value ranges may also be user accessible to allow for customization or editing thereof (e.g., for modeling different patient populations as needed).

The underlying information model incorporated within the application may provide key support for meeting the objectives described herein. Thus, the systems and methods of the present disclosure may build on prior work as described in Buckler, A. J., et al., Quantitative imaging biomarker ontology (QIBO) for knowledge representation of biomedical imaging biomarkers. Journal of digital imaging: the official journal of the Society for Computer Applications in Radiology, 2013. 26(4): p. 630-41; Freimuth, R. R., et al., Life sciences domain analysis model. J Am Med Inform Assoc, 2012. 19(6): p. 1095-102 and Buckler, A., et al., A Novel Knowledge Representation Framework for the Statistical Validation of Quantitative Imaging Biomarkers. Journal of Digital Imaging, 2013. 26(4): p. 614-629.

In example embodiments, data abstractions may be implemented in three ways: a knowledge graph, aka Resource Description Framework (RDF) triple/quad store, a relational database management system (RDBMS), and dictionaries in Python. FIG. 1 depicts the main classes that may be captured in Unified Modeling Language (UML), and FIGS. 2 and 3 identify key attributes for each class. The object model in FIGS. 1-3 further illustrates which classes are implanted on client and server sides, respectively, in preferred embodiments of the present disclosure.

Figure 2:
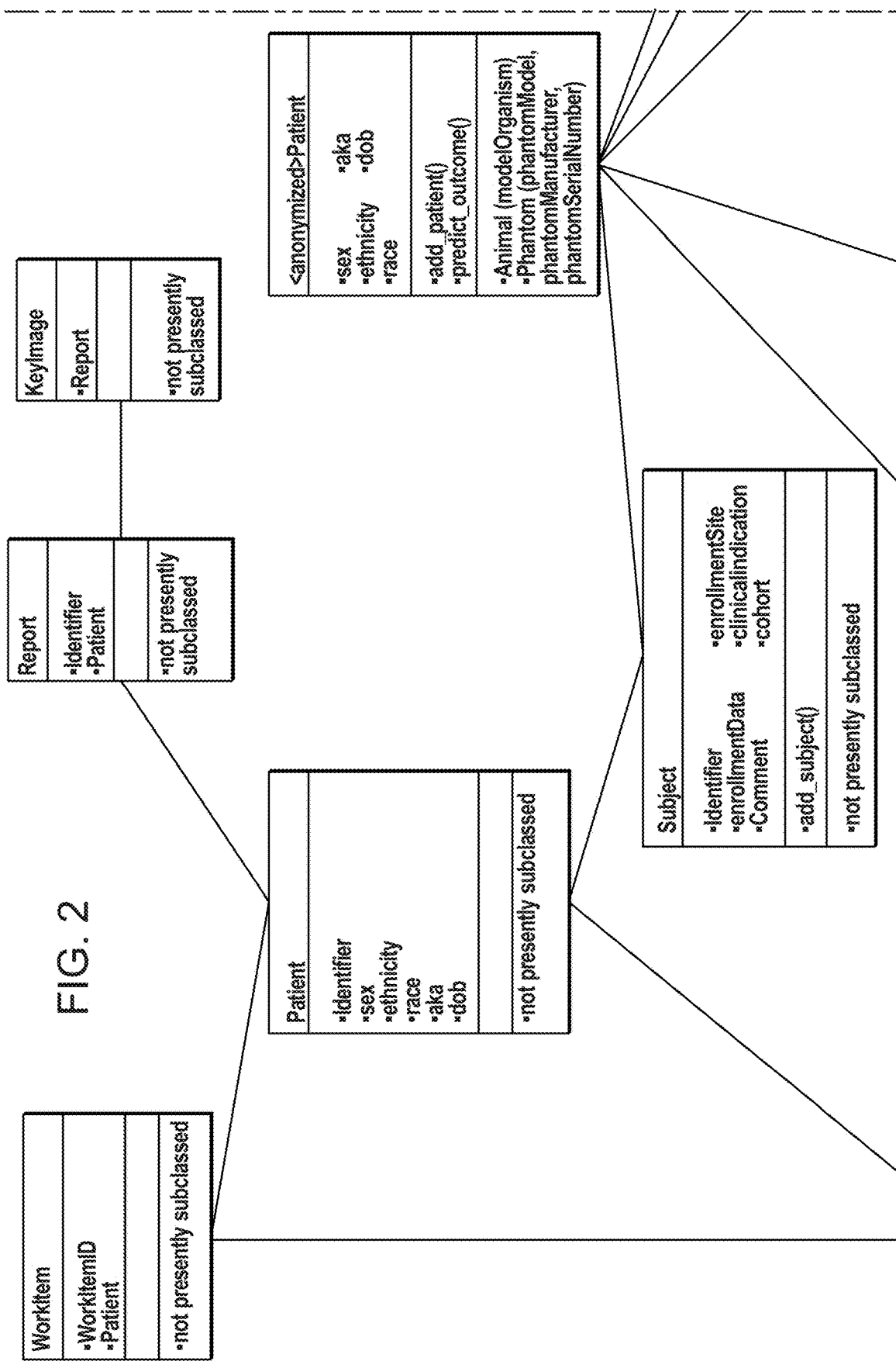
FIG. 2 is a magnified class diagram showing attributes (corresponding to upper part of FIG. 1)
Figure 2:
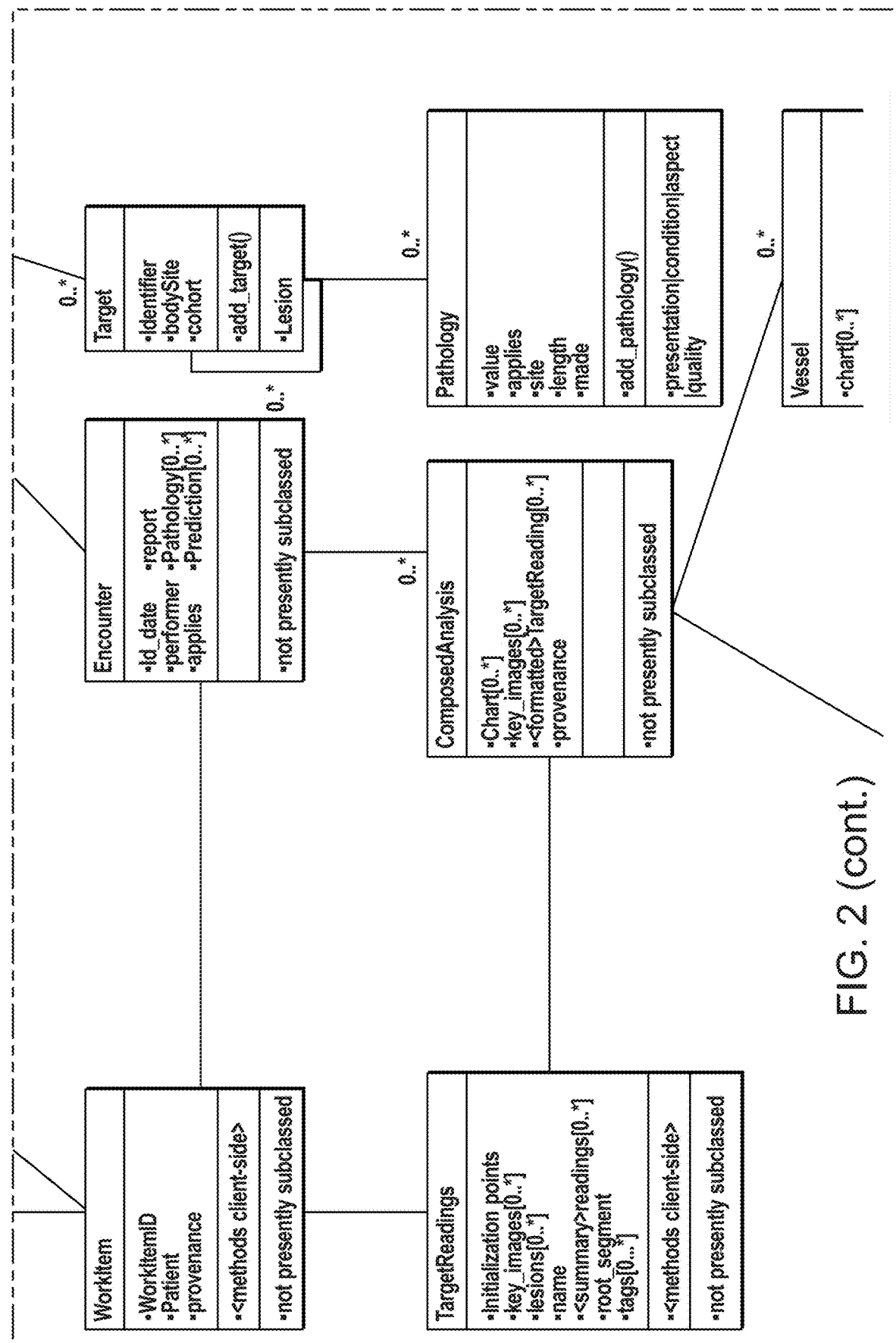
Figure 2:
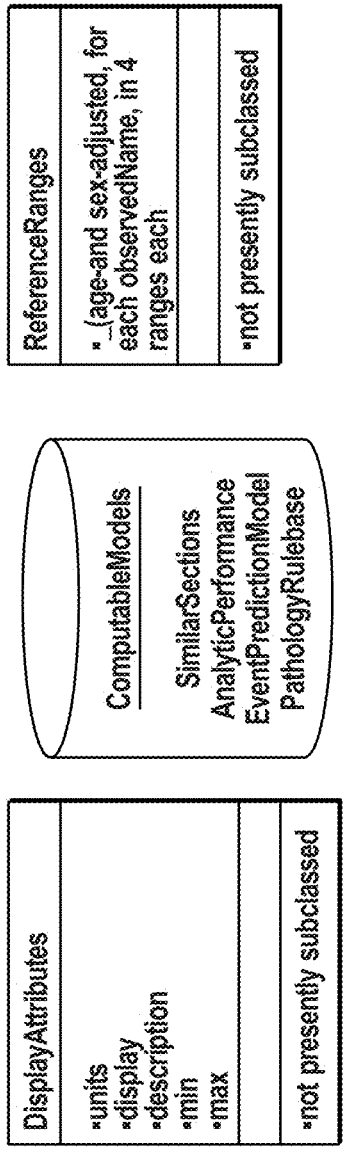
Figure 2:
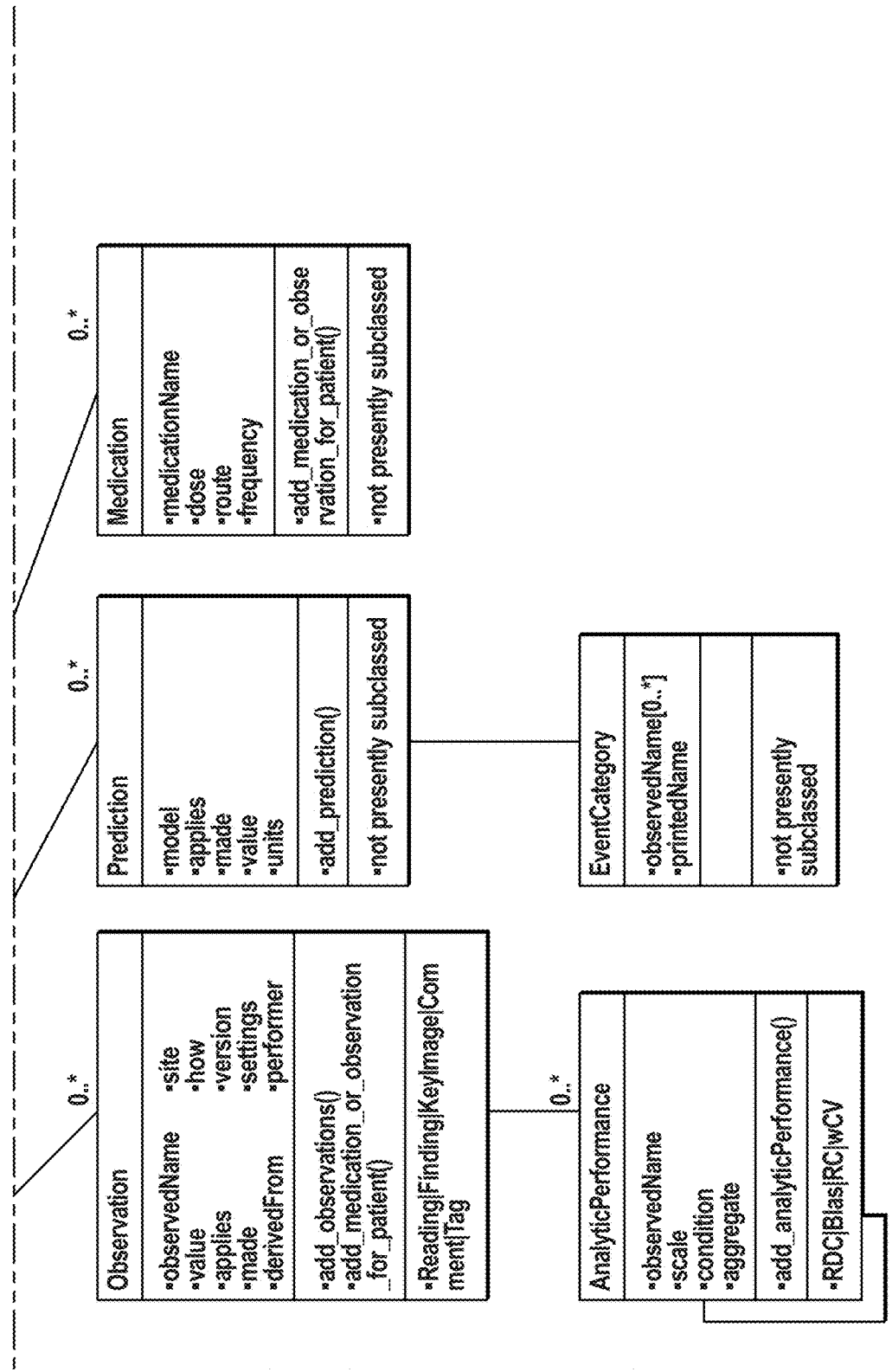
Figure 3:
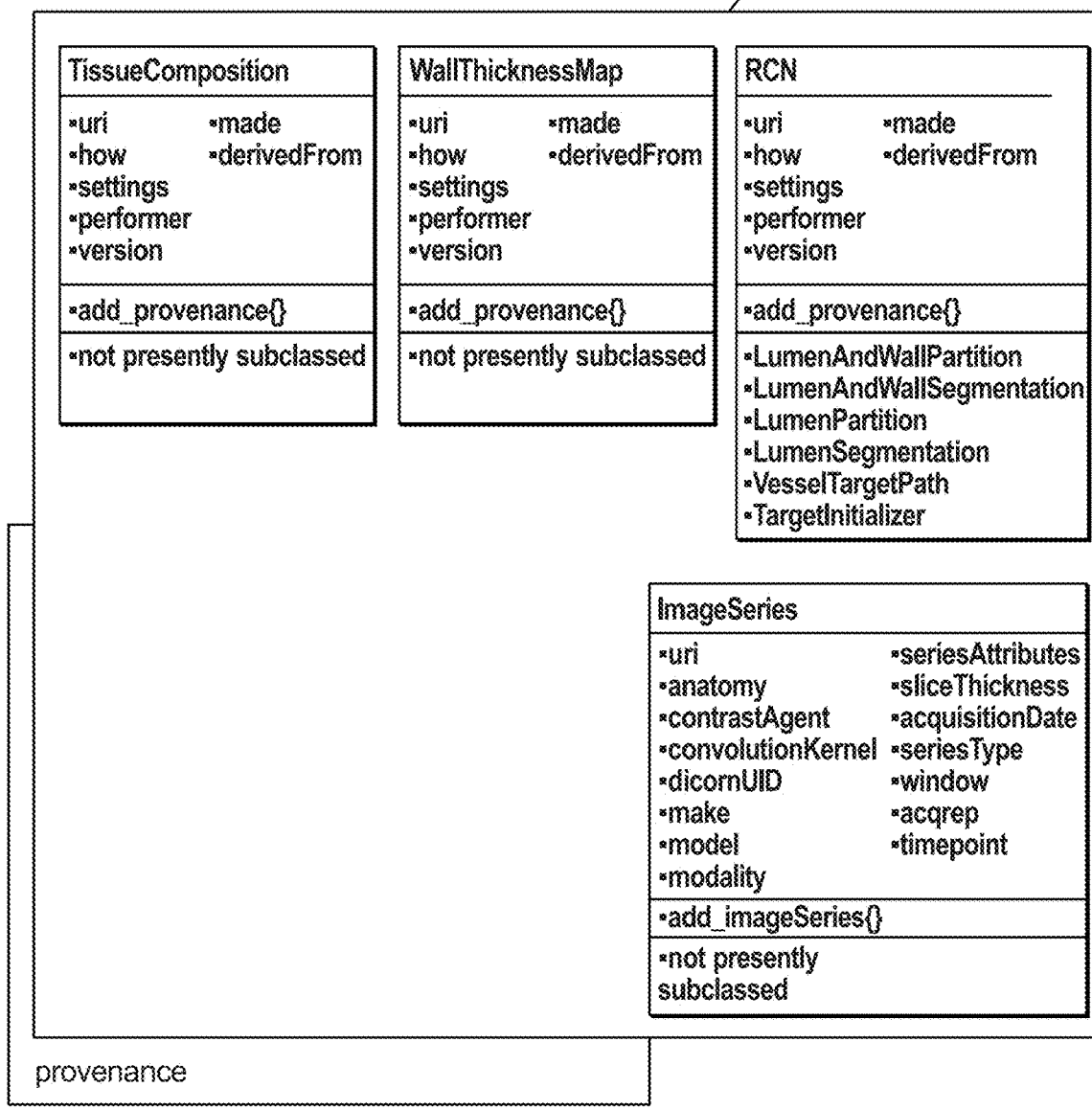
FIG. 3 is a magnified class diagram showing attributes (corresponding to lower part of FIG. 1.
Figure 3:
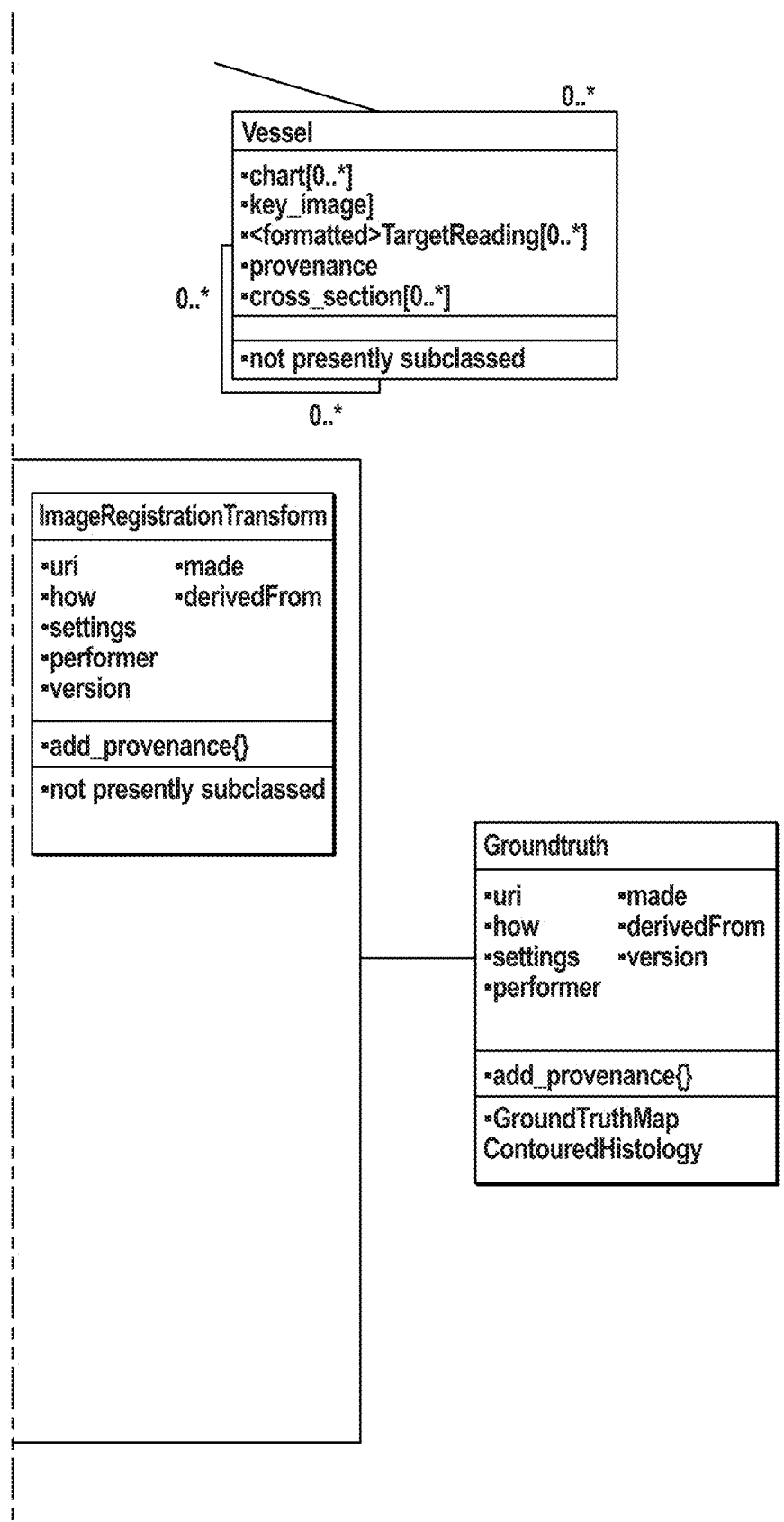

Furthermore, the object model in FIGS. 1-3 illustrates how data privacy and encryption may be handled in example embodiments of the present disclosure. The systems and methods of the present disclosure may utilize an ontology (built based on Quantitative Imaging Biomarker Ontology (QIBO)) as a hierarchical framework of terms that represents concepts for the quantitative imaging domain as well as key relationships between concepts. To meet HIPAA compliance requirements, Protected Health Information (PHI) may be stored in encrypted form, with one-way hash IDs being used in the non-encrypted discovery graph. A knowledge graph may then be utilized to expose SPARQL endpoints for discovery research. This design implements a strategy to protect individual identity of patients but yet still have access to quantitative information in such a way that relationships to specific patients are available for clinical care by clinicians with access rights. In general, "core identifiers" may be stored and accessed with encryption in the RDBMS, with "detailed" but non-identifiable information stored in the knowledge graph.

Figure 4:
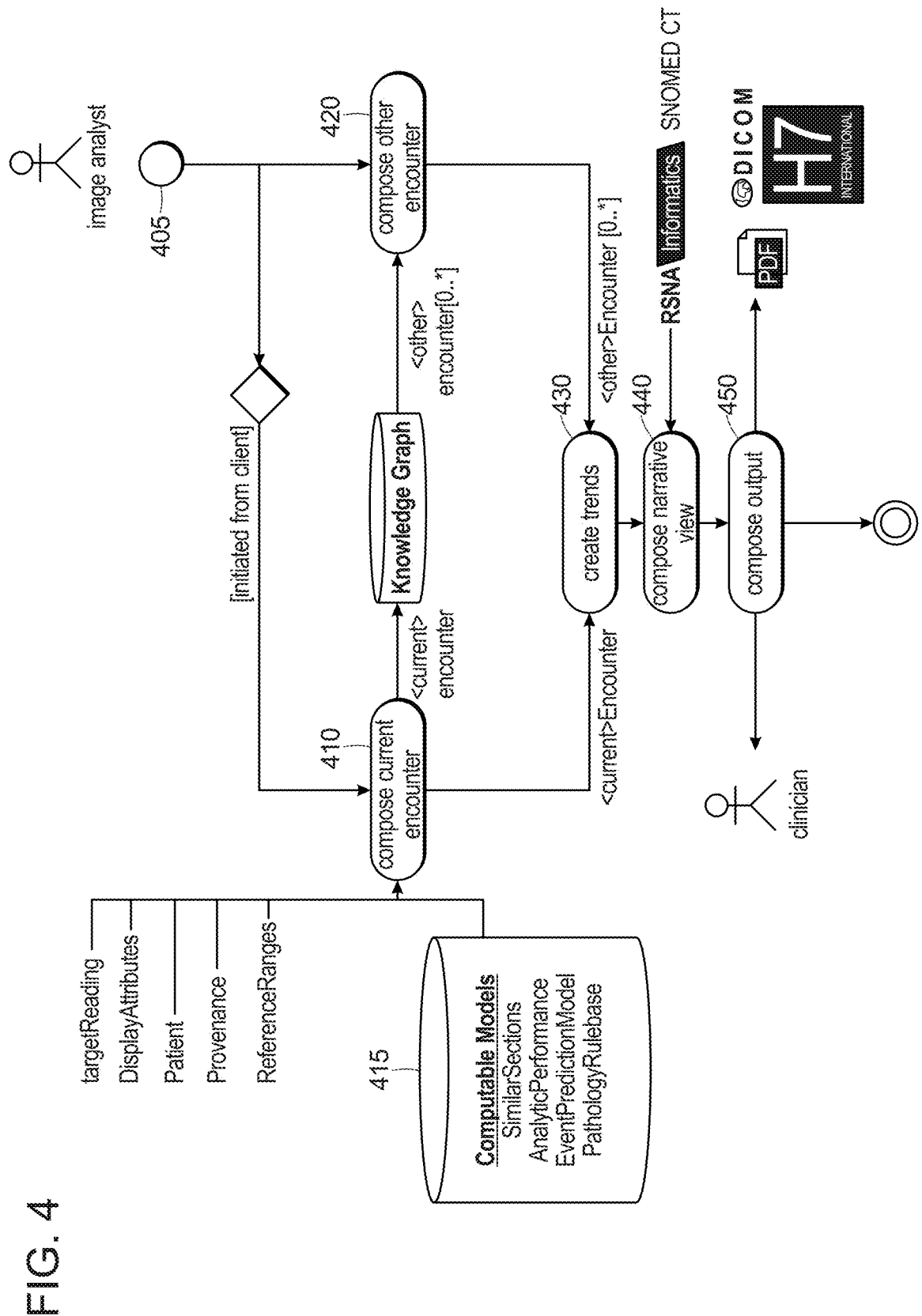
FIG. 4 is a schematic of main reporting activities and flow.

With reference now to FIG. 4, a high-level flow chart of an exemplary reporting module implemented by the systems and methods of the present application is depicted. Reporting is comprised of processing to compose a given patient's current encounter report 410 and processing of previously processed encounters 420 for longitudinal analysis. All encounters may then be used to create the trend analysis 430 if multiple encounters are found. The current encounter may then be taken and used to compose a narrative 440 as another way to view the current encounter's data. In some embodiments, a few sentences describing trends may also added to the narrative view (e.g., if a previous encounter has been found). In example embodiments, trend analysis provided by previous encounters may impact the narrative by adding context and/or by establishing a basis of comparison for current results. In some embodiments, a user interface may enable selection/customization of different types of narrative views.

A more detailed implementation of an exemplary reporting module implemented by the systems and methods of the present disclosure is discussed below. In example embodiments, a client application may perform image processing to make report content. A user may select a workitem file, whereby the client may securely package this data and transition to the server-side of the reporting module, obtaining an ID used in subsequent steps. The server may receive the hypertext transfer protocol (HTTP) multipart, store the issued report instance, potentially log a billing item ID to charge against, and return the report ID to the client which will be used to host the viewing/editing session as well as to provide continuity for maintaining versions and provenance. The server may start the processWorkitemThread, fork off external processes for "current" and "other" encounters, and ultimately send a HTTP(S) response back to the client. This advantageously allows "working ahead" on the server (even if the client does not request a report). Such working ahead provides for a near instant response one a report is queried since query analytics are precomputed and updated on the server side.

In example embodiments, when a user requests a report on the client side, the generate_context method may be called and process may generally be similar to the process flow described above for generating report content. In particular, generate_context may create (on the server side) a context data structure, which is passed to the web framework (Django, in an example) templates, which are then processed by the Django template processor. The output of that (HTML, CSS, and JavaScript) may be returned back to the client in a HTTP response. In some embodiments, a user may request a report be exported (e.g., to the client), whereby a 'download' request is sent to the server, which generates the HTML as above. The server may further convert the HTML output to PDF (which may then be added to both the knowledge graph and the RDBMS, e.g., implemented by Stardog and MySQL in examples, respectively). Once added to the knowledge graph, the PDF may then be downloaded to the client's local machine and also stored on the server's file system.

In example embodiments, a report module, according to the systems and methods of the present disclosure may utilize the following process flow to compose a current encounter (step 410). Image analyst data 405, e.g., taken from a file on the client, may be parsed into a hierarchy of anatomical fields of view relating to a target (e.g., target, vessel, and cross-section level blocks). Lesions, although subordinate to target in exemplary hierarchical models implemented in the file, may be brought up to be at the same level and in the same format as targets during this stage to enable separation of a target view and a lesion view. Predictions and pathologies may then be calculated. In example embodiments, composition of the current encounter (i) gets data from the workitem and readings files containing the measurements, (ii) parses the data, and (iii) stores all the data needed for the current encounter in a JSON file (as well as to the knowledge graph on export). Analysis target level measurements may be extracted in the file. In some embodiments, user marked lesions may be utilized in generating the output data. In other embodiments, automatic lesion detection and quantification may be utilized (e.g., in the absence of markings). Thus, lesion level measurements and cross-section level measurements, may also be extracted in the file. Thus, analysis of a current encounter, as stored in the output file, may ultimately create a composed analysis capturing the observation hierarchy into a series of numeric and visual artifacts. In some embodiments, analytics may further apply predictive models at the patient level. The systems and methods of the present disclosure have high repeatability and accuracy. By virtue of having objectively assessed analytic/technical performance, as well as all detailed provenance, all observations are supported by a detailed audit trail of what they were based on, who processed steps, how the steps were undertaken, the settings and tool versions used, and detailed performance metrics of the uncertainty of the observed value.

In example embodiments, pathology determination includes derivation of presentation, based on nearby or related pathologies as needed (e.g. the post-stenotic dilatation), setting up the abstractions needed for the natural language narrative, and storing findings in the knowledge graph with reference to applicable biophysical concepts. These stored findings may advantageously provide for the composition of the narrative view, which in example embodiments, operates by automatic composition of key images, clinical indication, procedure, findings from the pathologies detected represented in natural language, and initializes an impression based on the patient-level predictions. Drill downs may be made available (e.g., via a user interface) for lineal graphs of measurements along the vessel's centerline and for cross-section measurements, reference ranges, and similar sections.

In further example embodiments, a report module, according to the systems and methods of the present disclosure may utilize the following process flow to compose other encounters (step 420) and create trends (step 430). As previously noted, in some embodiments, the reporting module may use the knowledge graph to retrieve information across multiple encounters, thereby enabling a longitudinal trend analysis, e.g., of given identified lesions or targets, as well as enabling summary measures for the patient as a whole. Analyzing previous encounters has the same general process flow as analyzing a current encounter except that the data is queried from the knowledge graph and nothing is calculated. Encounters that had previously been exported from the client will be found if present. These previously analyzed encounters may then be composed in a format consistent with the current encounter (if necessary). Each encounter (current and past) may advantageously, presented on its own tab in the Chart view.

In example embodiments, analytics may include multiple, numeric trend lines with the encounters composed into graphs. For each measurement discovered that has more than one encounter, a plot may be created at target, lesion, and vessel levels. Like the encounter tabs, there may be a target view and a lesion view. As previously noted, the encounters and trends may also be used for generation of descriptions of change in the Narrative view.

In further example embodiments, a report module, according to the systems and methods of the present disclosure may utilize the following process flow to compose a narrative view (step 440). Pathologies and predictions from a current encounter may be used to create summary statements, based in quantitative data but expressed in natural language, to express the measurements. In example embodiments, the measurements may be categorized to determine, e.g., for each cross-section, if they are clinically relevant. Clinically relevant measurements may then be presented, e.g., with clinically relevant cross-sections categorized into a lesion. Data structure with age-adjusted normal ranges, as in the following illustrative example, are shown in Table 1.

TABLE 1

| observedName | 0 | 1 | 2 | 3 |
|---|---|---|---|---|
| MaxStenosis (worst of by area or diameter) | 0-29<br>No text | 30-69<br>"moderately stenosed" | 70-99<br>"severely stenosed" | 100<br>"Fully occluded" |
| MaxDilation (worst of by area or diameter) | 1-1.2<br>No text | 1.2-1.5<br>"mildly dilated" | 1.5-2.5<br>"moderately dilated" | >2.5<br>Severely dilated |
| MaxWallThickness | 0-1 mm<br>No text | 1-1.5 mm<br>Mildly thickened | 1.5-2.5 mm<br>Moderately thickened | >2.5 mm<br>Severely thickened |
| MaxCALCArea | Lower quartile<br>No text | Some calcification | Moderately calcified | Upper quartile<br>Highly calcified |
| MaxLRNCArea | Lower quartile<br>No text | Some lipid deposits | Moderate lipid core | Upper quartile<br>Large lipid core |

Pathologies are based on the table of reference ranges that can be changed by the user, via a rule-based approach (Pyke, in an example) that determines presentation or condition, aspects, and qualities, each of which is listed for use by the natural language generation step as grammatical elements.

An illustrative example of rules pertaining to measurements that have been categorized can be understood broadly in the example shown in Table 2.

TABLE 2

| When . . . | | | | | |
|---|---|---|---|---|---|
| Max Stenosis | Max Dilation | MaxWall Thickness | Max CALCArea | Max LRNCArea | Use |
| 0 | 0 | 0 | 0 | 0 | Normal |
| 0 | 0 | ≥1 | | | Outwardly remodeled plaque without stenosis |
| 0 | ≥1 | 0 | | | Dilitation |
| 0 | ≥1 | ≥1 | | | Outwardly remodeled plaque with dilation |
| ≥1 | 0 | 0 | | | stenosis |
| ≥1 | 0 | ≥1 | | | plaque with stenosis |
| ≥1 | ≥1 | 0 | | | (cannot happen) |
| ≥1 | ≥1 | ≥1 | | | (cannot happen) |

Other rules support chaining for elucidation of relationships, not just thresholded measurement categories.

Presentations and conditions are treated as noun phrases for sentence subjects, where a presentation is countable (e.g., "an atheroma", SNOMED-CT 50808002) and a condition is not countable (e.g., "vasculitis", SNOMED-CT 31996006). Qualities are adjectives in the subject noun phrase, with an optional adverb (e.g., "highly calcified"). Aspects are coordinated objects, grammatically noun phrases with preposition (e.g., "with a large lipid core"). These are used in paragraphs for each lesion in the findings section, where the topic sentence specifies body site, center, and length. If there is no detected pathology, a paragraph may be generated indicating that the target presents as normal. These grammatical specifications are used as input to a natural language generation library (simplenlg, in an example). In general, the narrative may present abnormal findings or, if no abnormal finding are present, may indicate such. By highlighting only the abnormal findings in the narrative, the narrative advantageously presents only the most clinically relevant aspects of the data included in the chart view. In example embodiments, narrative "Findings" may be presented via a user interface, e.g., in an edit window, for a user to accept, modify, or change outright. Tools may also be provided to enable a user to refine the narrative generation process, including terminology, presentation format, included findings, preferred metrics, etc.

A few representative example outputs which may be represented in the "findings" block of a report, are as follows.

If the patient only has no lesions marked:

"The left carotid presents with 28.0 mm of atheromatous plaque centered in the bifurcation. The highly dilated, highly calcified atheromatous plaque has severe remodeling and a large lipid core. The lesion is likely a type IV or V plaque by the AHA classification system."

If there was a lesion marked:

"The lesion xyz in the left carotid presents with 18.5 mm of atheromatous plaque centered 5.5 mm distal from the bifurcation. The highly dilated, highly calcified atheromatous plaque has severe remodeling and a large lipid core. The lesion is likely a type VI plaque by the AHA classification system. Maximum stenosis lies outside of the lesion in the common carotid, 3 mm proximal from the bifurcation, outside of where xyz has been marked."

Or for a different patient:

"Patient MRN0000 presents normal for a 56 year old man."

Example outputs represented in the "Impression" block of the report, and presented in an edit window for the user to accept, modify, or change outright, are as follows (illustrating the output when two different prediction models are installed, one called "stroke" and the other called "neuro"):

If there was only one encounter:

"These findings confer a 76% likelihood of the patient experiencing ischemic stroke or TIA according to the stroke model."

"These findings confer a 70% likelihood of the patient experiencing a recent ischemic stroke or TIA according to the neuro model."

If there were multiple encounters:

"Patient MRN000 was seen 3 years prior to the present encounter. Overall plaque burden increased by 120%, with lesion xyz growing 2 mm in length. In 2011, the most clinically vulnerable presentation 6 mm distal to the bifurcation was most likely type IV, but this location is now more likely a V, and other cross sections have progressed."

"These findings confer a 70% likelihood of the patient experiencing a recent ischemic stroke or TIA according to the neuro model, an increase of 4% relative to 09-06-2011."

In further example embodiments, a report module, according to the systems and methods of the present disclosure may utilize the following process flow to compose an output (step 450). The report generator is accessed either when an analysis is first performed in the client, or if an existing report is updated in the browser. Using Django, for example, a context of all previous steps is put into HTML templates to create the page. The Chart view report is organized into hierarchical observation contexts. The following elements comprise the report for each available encounter:

Patient-level summaries (demographics, target list, medications and observations)

Target-level analysis (key images, tables, graphs, lesion list)

Vessel-level analysis (key images, tables)

Cross-section-level analysis (key images, tables, graphs, reference ranges, similar section plaque type chart)

As noted above, in some embodiments, more than one encounter may be available. Thus, in some embodiments, a user interface may present a "Trends" tab with trend charts for each calculation at each observation context. Comment fields and provenance (audit trails) may advantageously be included at all levels. In preferred embodiments, the report module may generate as output an HTML page that can be edited and/or an export file (such as a PDF). In some embodiments, the outputted report may implement the Digital Imaging and Communications in Medicine (DICOM) Structured Reporting (SR) Patient/Study/Series information model. In some embodiments, hierarchical observation contexts may add a hierarchical tree of "Content Items" with coded nomenclature which allows use of vocabulary/codes from non-DICOM sources (e.g., RadLex Logical Observation Identifiers Names and Codes (LOINC®) and SNOMED-Clinical Terms). RadLex provides standardized indexing and retrieval of radiology information resources. It unifies and supplements other lexicons and standards, such as SNOMED-CT and DICOM. Using RadLex terms, it provides a standardized information model compatible with DICOM SR, XML, and Health Level 7 (HL7) formats for such observations. In example embodiments, templates may be used to define content constraints for specific types of documents/reports. Relationships between a given report, the subject of the report, the observer making the report, related or supportive data, and the observations themselves may be represented in the RDBMS and may be output using rationalized concepts of DICOM SR with those of HL7 Clinical Document Architecture (CDA) (DICOM PS3.20 2016c—Imaging Reports using HL7 CDA). The HL7 CDA is an XML-based markup standard intended to specify the encoding, structure and semantics of clinical documents for exchange.

Query for patient information used to augment imaging predictors in predictive models, as well as means by which report data is exported to Electronic Health Record systems (EHRs), may be performed using python-hl7 which is a library for parsing messages of HL7 version 2.x into Python objects. python-hl7 includes a client that can send HL7 messages to a Minimal Lower Level Protocol (MLLP) [121] server also implemented in the library.

Computational models (415) may be utilized for initializing reference ranges. For example, reference ranges for biological properties may be initialized at least in part from histology (however, may be overridden by the user, and similar section analysis of phenotypes). Reference ranges may also be initialized at least in part based on analytic/technical performance from reference and ground truth collections (allowing representation of uncertainty drawn from analytic performance calculations). Furthermore, reference ranges may be initialized at least in part from outcome prediction models based on model building techniques.

Figure 5:
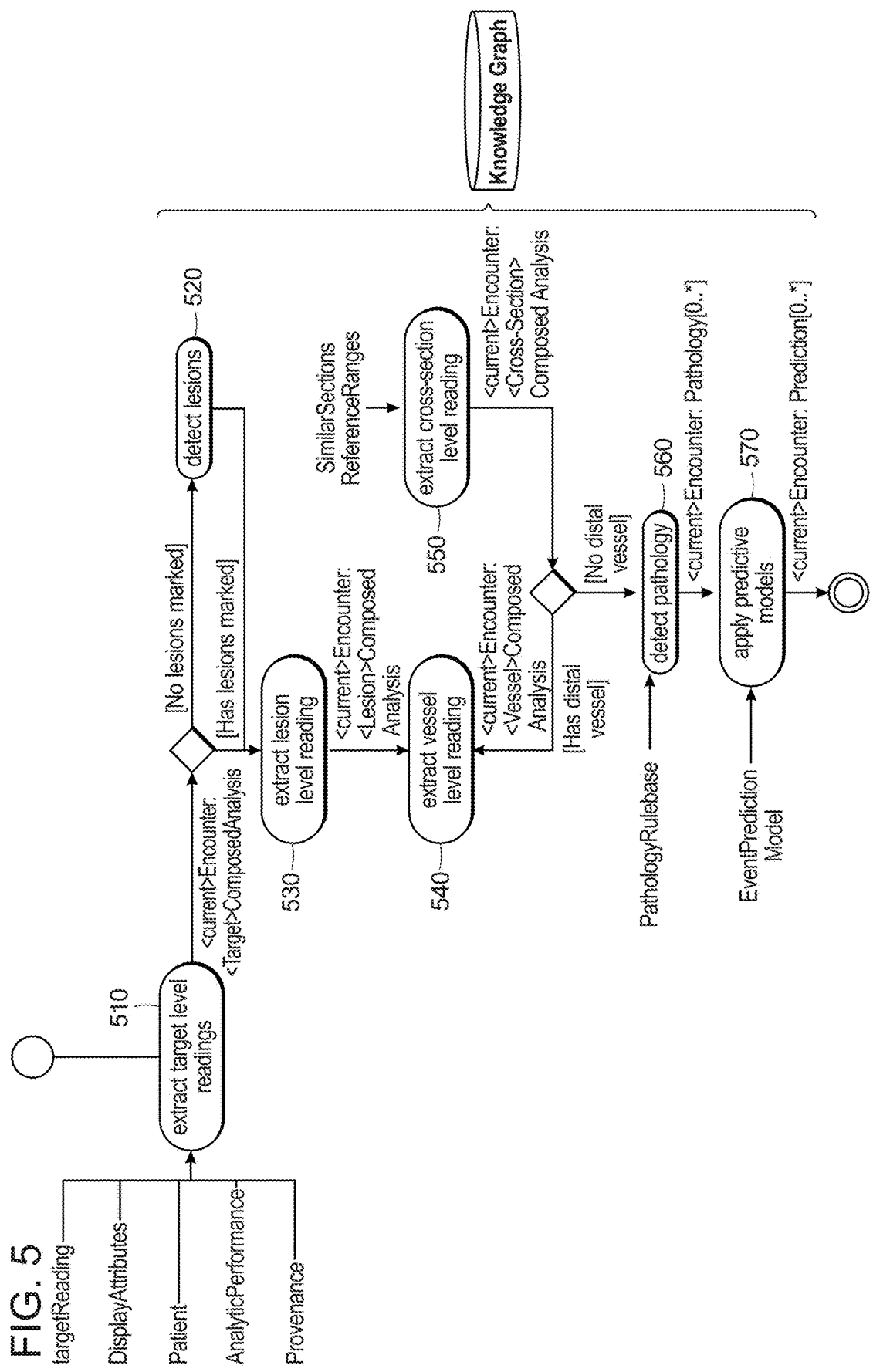
FIG. 5 shows a further breakdown of processing the current encounter.

Composing a current encounter (e.g., step 410 of FIG. 4) is further illustrated and described with respect to the exemplary process flow of FIG. 5.

At step 510, top level measurements are added to the current encounter, and added to a knowledge graph if on an export. The measurements may be sorted into either structure or composition tables.

At step 520, lesions are detected. In example embodiments, lesions may be marked by a user, e.g., based on a user selected area or region of an image, and/or based on a user confirmation of suggested lesion regions. If no lesions have been marked by the user, lesions may be determined based on a combination of the measurements. In example embodiments, areas of interest may be determined using ranges initialized based on cohorts of patients for quartiles, however they can be changed by the user. If there are multiple high measurements or one very high measurement, this will be included in what will be determined as a lesion.

At steps 530, 540 and 550, lesion, vessel, and cross-section level measurements may be respectively extracted. For all lesions found or marked within the target, the same flow is followed as for the target level measurements. Vessels in the target are recursively looped over, starting at the root vessel. The same flow is followed as for the target-level measurements. The cross-section level has all the of the same data elements taken out as with the target or lesion, but also presents measurements using reference ranges and computes a similarity metric relative to a collection of potentially similar sections that have been annotated with a known phenotype. In addition to adding the section to the target, the cross-section level also is added to any lesions that contain it. These measurements are also used to create various sets of plots to be displayed at the target/lesion level to show the progression along the target/lesion.

At step 560, pathology may be detected. Using a rule-based system on the lesion level measurements, pathologies are then determined. The same ranges as with detecting lesions are used. If detected on an export, they are added to the knowledge graph. The rule base utilizes both forward and backward chaining to determine the overall presentation or condition, aspects, and qualities, each of which is listed for use by the natural language generation step as grammatical elements. For example, atheroma is detected as signified by a thickened wall with moderate or more lipid-rich necrotic core, and regardless of calcification, stenosis, or remodeling ratio, as distinct from vasculitis, signified by thickened wall without appreciable lipid-rich necrotic core or calcification but regardless of stenosis or remodeling ratio.

At step 570, predictive models may be applied. R models created by a statistician are then called with the target and lesion level measurements. These outputs are used in the Narrative view under the "Predictions" section. In addition to the current encounter's predictions, any previously exported predictions found would be added to show the change in prediction. The predictions are added to the knowledge graph when exported.

Figure 6:
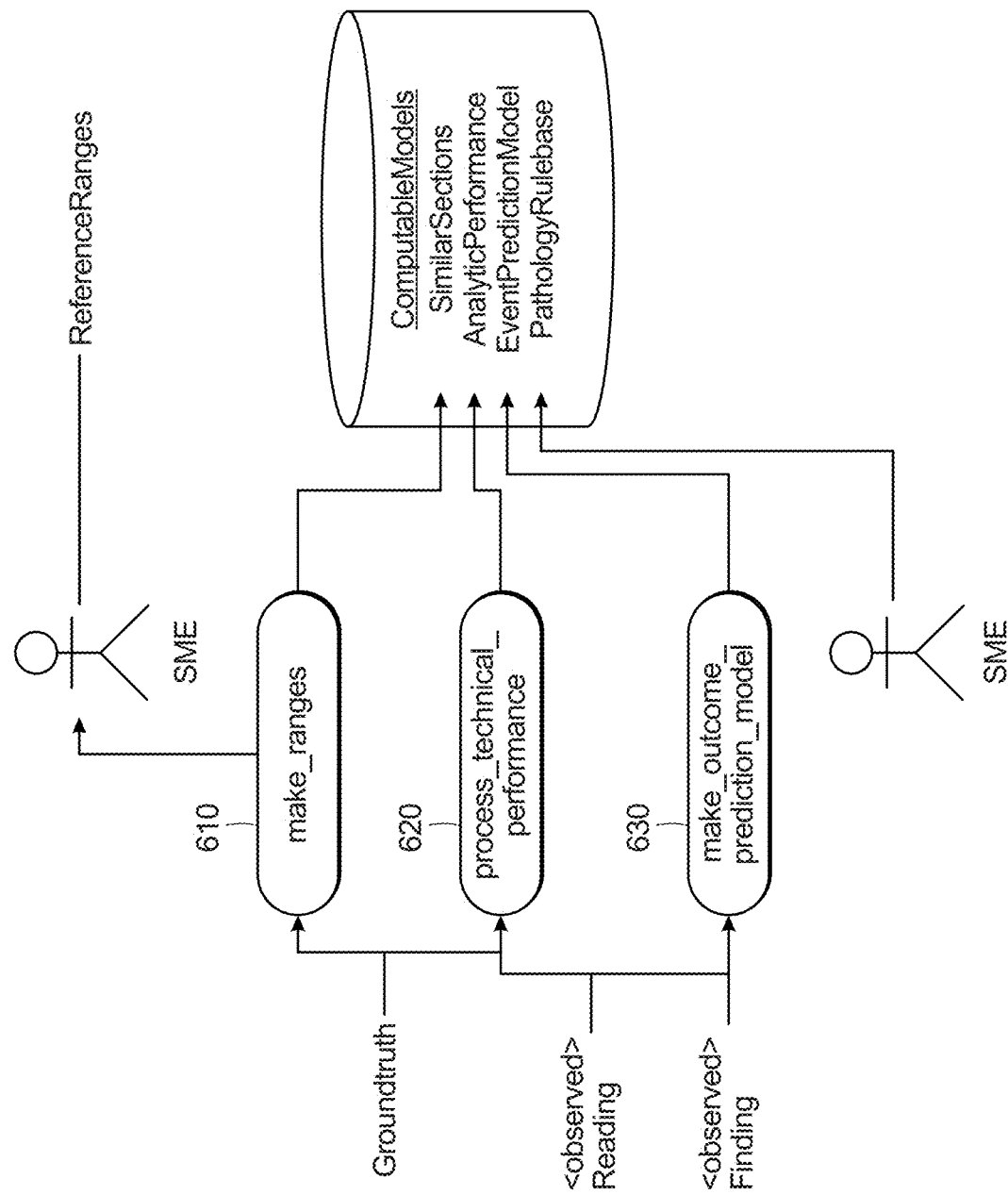
FIG. 6 illustrates decomposition of prepared computational models.

With reference now to FIG. 6, an exemplary process flow for preparing computational models (e.g., computational models 515 of FIG. 4) is described.

At step 610, reference ranges are constructed. Ground truth or reference data from defined patient cohorts is analyzed to determine distributions of values, annotated by age and sex as well as compilation of measurements vectors that may be used for comparison purposes, e.g., to enable determination of how similar a given imaging cross-section is to a set of reference sections.

At step 620, technical performance is processed. All measurements in the knowledge graph are queried out and statistical analyses of analytic or technical performance are created, including, for example, estimation of basis, linearity, reader variability, and limit of quantitation. A variety of charts and graphs are produced, but from the perspective of the reporting applications, a data structure for each type of measurement is produced that enables given values to be represented on user request (e.g., right clicking the number) with a confidence interval to represent measurement confidence.

At step 630 predictive models are constructed. On the basis of observed measurements and outcome findings, predictive models are created for use in applying a given patient's measurements to determine predictions for outcomes.

Additional capability is provided for tracking and display of detailed provenance for audit trails, ability for selection of product (allowing functionality for multiple regulatory jurisdictions to be present in the same code base), and user-institution binding. The view session has the facility to trap an export signal and store the returned PDF, DICOM S/R, HL7 CDA, or other formatted result to disk or transfer to EHR. Likewise, the CAPgraph server can also be accessed from a browser. From the browser, a user can view the reports that have been exported. The user can also 'Update' the report to get back to HTML, and re-export the updated report as a PDF. These capabilities are further implemented in a manner that allows precomputation while other aspects of the image processing are taking place for efficient and nearly instant availability of results from the user's point of view. All functions are password protected, transfers of protected health information are encrypted, and users may have one or more institutional affiliations for billing purposes and in filtering report listings.

Figure 7:
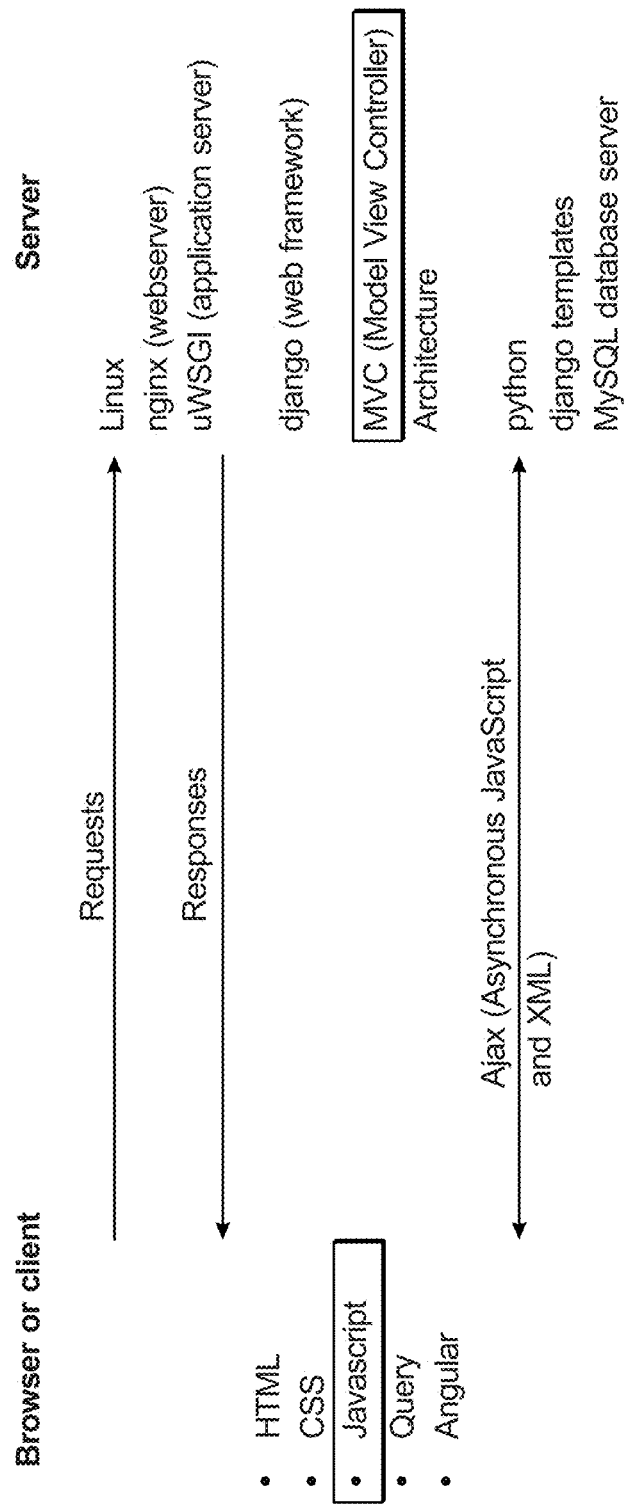
FIG. 7 is a schematic illustration of a client-server architecture.

With reference now to FIG. 7, in exemplary embodiments, the flow process of implemented by the reporting module may advantageously be decomposed into a client side and server side. The data flow between the vascuCAP client and CAPgraph server is as follows.

When a user selects a workitem file on the client:
1. A 'workitems' HTTP request is sent to the server
2. That is handled by the 'workitems' view in the server
3. That starts the processWorkitemThread, which processes the multi part message containing the workitem file, the readings file, and the images.
4. Next, it forks off 2 external processes: generate_current_encounter_data.py, and generate_other_encounters_data.py
5. generate_current_encounter_data gets data from the workitem file and calls readings_module.VesselTree.from_file. It passes the data returned from that to fix_blocks, and then stores all the data needed for the current encounter in a JSON file.
6. generate_other_encounters_data gets data from the linked data store (implemented by Stardog in an implementation) and calls readings_module.Vessel- Tree.from_CAPgraph. It passes the data returned from that to fix_blocks, and then stores all the data needed for the other encounter in a JSON file.

7. A HTTP response is sent back to the client.

When a user requests a report on the client:
1. A 'workitem' request is sent to the server.
2. That is handled by the 'workitem_reading_tree_resource' view in the server.
3. That calls 'generatereport.py' passing in the JSON data generated above.
4. That causes the generate_context method to be called, which creates a context data structure, which is passed to the django templates, which are then processed by the Django template processor.
5. The output of that is HTML, CSS, and javascript, which is all returned back to the client in a HTTP response.

When a user requests a report be exported on the client:
1. A 'download' request is sent to the server.
2. This is handled by the download method of generatereport.
3. That generates the HTML as above, however it then converts that to PDF.
4. At this point, data is added to both the linked data store and the RDBMS.
5. The PDF is downloaded to the client's local machine and also stored on the server's file system.

The CAPgraph server can also be accessed from a browser. From the browser, a user can view patients who have had reports exported, view those reports as PDF, 'update' the PDF back to HTML, and re-export the updated report as a PDF. Each of these functions is implemented by sending a request from the browser of type patients, reportlist, instancelist, update, or download. They are handled by functions of the same name. Each function extracts the requested data from the RDBMS and formats it for presentation in the browser.

With reference to FIGS. 8-15 an exemplary report generated using the systems and methods of the present disclosure is depicted along with an exemplary user interface for interacting with the report.

FIG. 8 depicts the top of the Chart view for the report of FIG. 8-15. This view contains a tab representing the encounter used to generate this report, sequenced chronologically with any other encounters found to have been previously exported for this patient. Other encounters for the same patient, if they have been previously exported, will be displayed as tabs, and a Trends tab will be available across them. Notably, if there is only one encounter available, there will be a single tab labeled by date and no "Trends" tab displayed.

The report may be viewed at either the Target-level, or at the Lesion-level via a toggle at the top to switch views. If lesions have been marked, it will default to Lesion-level, otherwise it will default to Target-level. The Lesion-level Report contains the same features as the Target-level Report. However, the calculations and graphs are determined by the lesion boundaries.

Figure 9:
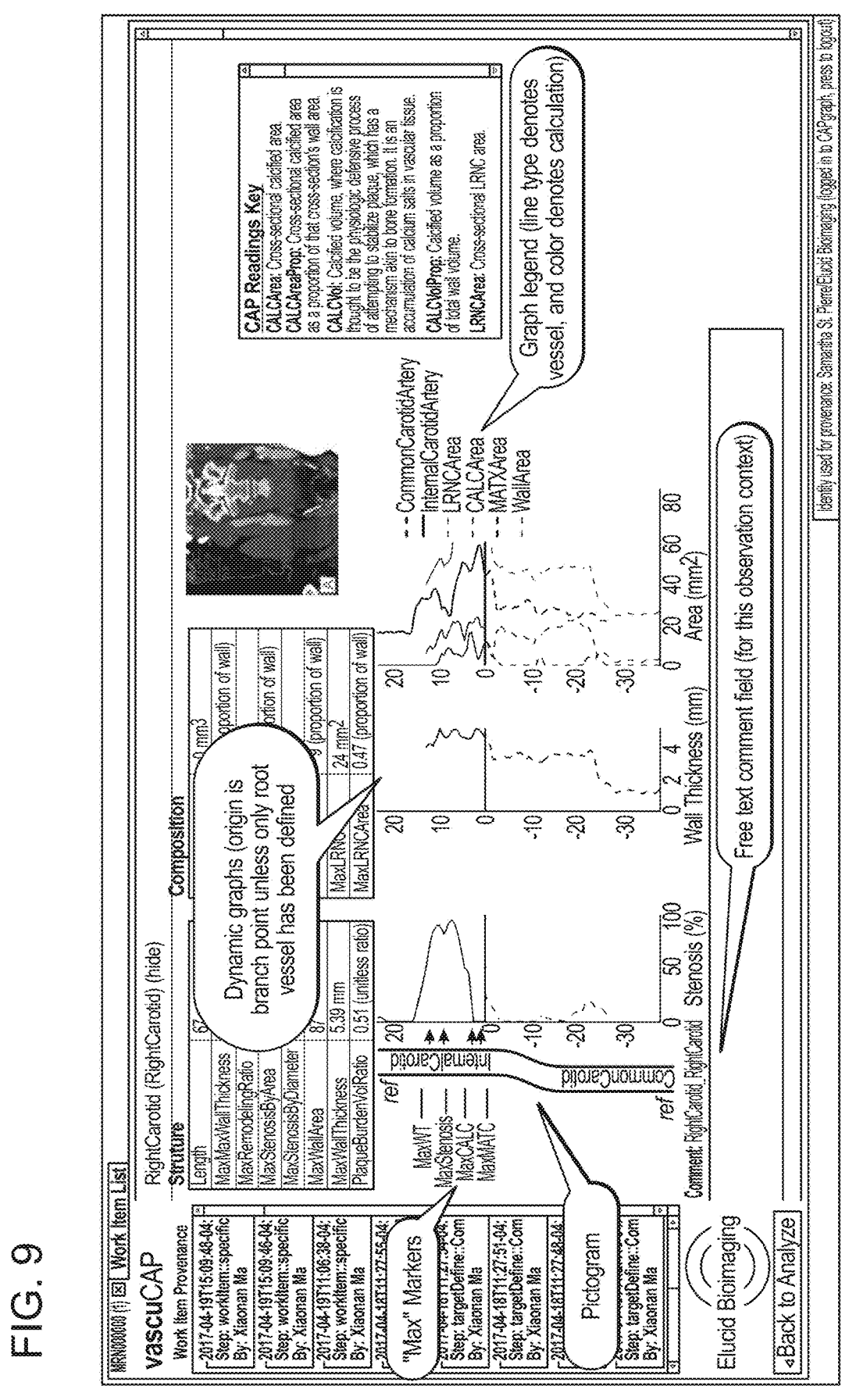

As depicted in FIG. 9, a user can scroll down through the Chart view of the report to see as many graphical contexts as present in the target. Recording key images at the cross-section level will also determine the default state of the show/hide functionality (that is, a cross-section is defaulted to be shown if it has a key image and by default hidden if it does not). Cross sections with max target level measurements will automatically have a key image taken. To expand the target analyses, a user clicks on the Show/Hide button next to the target(s), vessel(s), and cross-section(s) of interest, regardless if initially shown or hidden. Cross-sections are subordinate to vessels, and vessels to target, so expanding a target will expose the vessels within it and expanding a vessel will expose the cross-sections within it (FIGS. 10 and 11, respectively).

Figure 11:
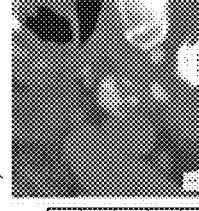
FIG. 11 is a screen shot of cross-section level detail (hierarchically organized under vessel or segment)

As depicted in FIG. 11, by scrolling lower through the Chart view, a user sees as many cross-section contexts as present in the vessel. Structure and composition calculations for this cross section may be shown on graphs indicating ranges normally seen in a subpopulation. A bar chart may be presented where the height of the bar indicates a normalized count of cross sections which meet similarity criteria and for which American Heart Association (AHA) classification type for atherosclerotic plaque has been determined from histology. The "Show/Hide" controls are defaulted based on the presence of key images as had been added in Encounter Analyze, but additional observation contexts may always be shown and whatever is shown may be hidden.

Figure 12:
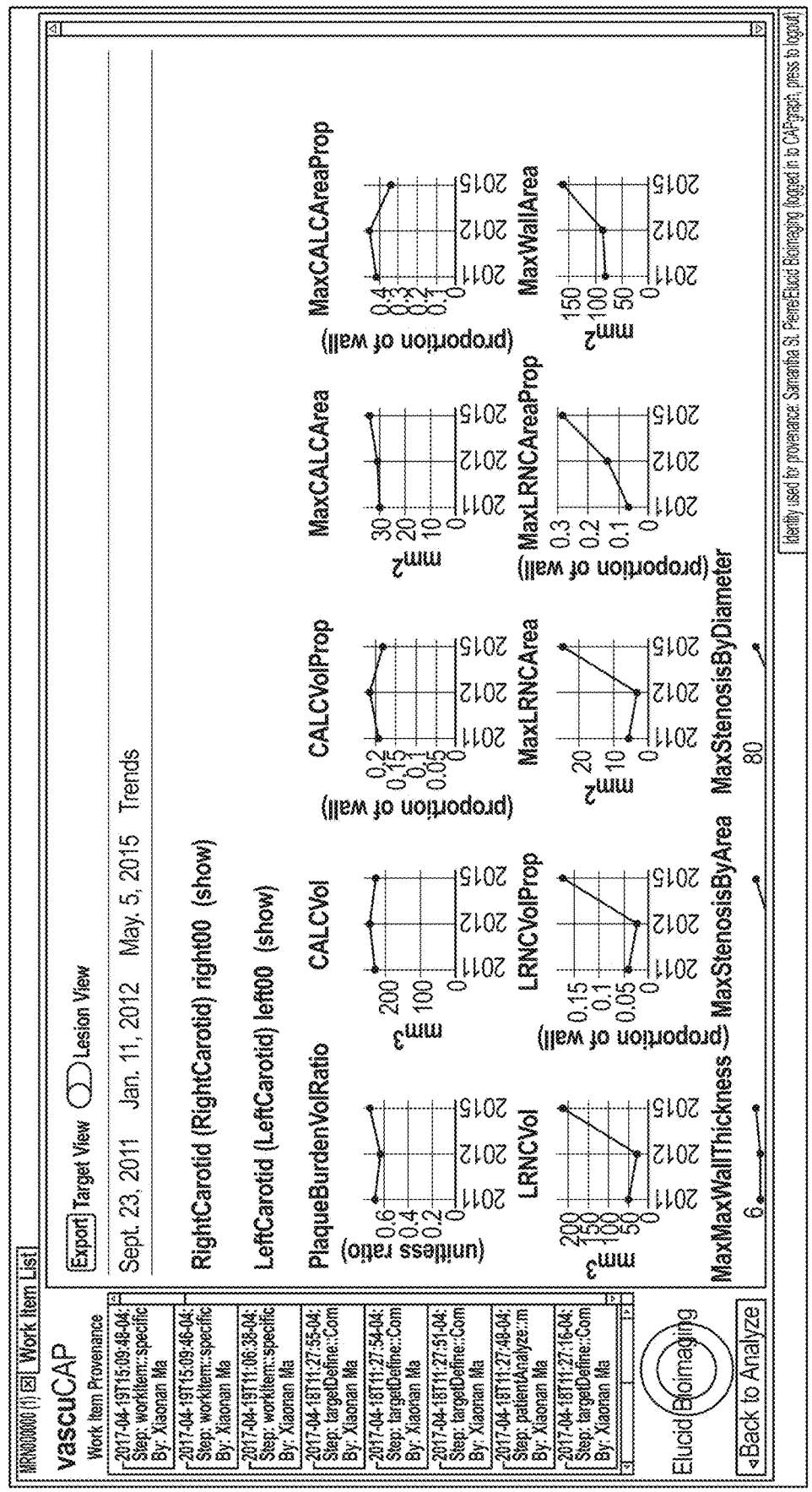
FIG. 12 is a screen shot of a presentation of longitudinal change across encounters.

As depicted in FIG. 12, longitudinal trends charts for patients with multiple encounters may be accessed by pressing the Trends tab at the top of the Chart view. Clicking on any measurement brings up both the numeric confidence interval inclusive of bias and precision due to a variety of sources of error and variability, as well as the detailed audit trail of how the measurement was derived (FIG. 13).

FIG. 14, depicts an example narrative view corresponding to the Chart view of FIGS. 8-13. The Narrative view is structured to look more similar to a traditional radiology report but backed by the quantitative data. It has sections for Clinical Indication, Procedure, Findings, and Impression. These fields are initialized by the processing described above, but presented in edit boxes prior to export. Drill downs are presented with show/hide buttons, which are initially hidden but capable of being shown on selection. The narrative view depicted in FIG. 14 is an exported version thereof.

With reference again to FIG. 8, to export the analysis results to the discovery knowledgebase and create a composed PDF report to document the analysis, a user presses the Export button at top. When the Export button is hit, only those contexts that are shown are included in the PDF, but if a subsequent Update is performed, they are still available. A browser access is provided with multiple levels of search fields to access exported reports, which also enables an Update function that allows a given report to be updated by the same or a different clinician after the initial export, maintaining a rigorous provenance record of changes made (FIG. 15).

Both supporting this and in turn being retained as persisted linked data left in the knowledge graph afterwards, SPARQL and other batch processing/discovery applications support inference for data mining and other capabilities beyond the report itself [38-40]. This representation provides a direct benefit in allowing integrated knowledge across imaging and non-imaging data sets, enabling applications to assemble/transform the set of RDF triples to SPARQL queries. This enables data integration across the genomic, gene expression, clinical phenotype and imaging data, using federated SPARQL queries and inferencing to formulate testable hypotheses and associated datasets for the validation of a new imaging biomarker based on a linked data specification of the biomarker.

Many advantageous features are disclosed by the systems and methods presented herein. For example, the subject application provides for a novel reporting engine integrated with quantitative imaging application software that integrates reporting logic to a rich data representation based on ontology. Furthermore, the subject application provides for an expressive natural language interpretation of underlying objective and quantitative measurement data. Thus, in some embodiments, systems and methods may include drill down capability highlighting the specific pathology tied to the narrative findings. Furthermore, the subject application, provides a hierarchically organized detailed chart with varying levels of summarization reaching down to a level which would otherwise only be available ex vivo but which by this method is accessible non-invasively in vivo. For example, a hierarchical characterization of the target anatomical site is provided which includes characterization of a vessel, a vessel segment, and a segment cross-section.

Other advantages disclosed herein include:
- When a user selects a workitem file on the client, starts the processWorkitemThread, forks off 2 external processes for current and other, ultimately sends HTTP(s) response back to the client. This is the process that allows "working ahead" on the server.
- When a user requests a report on the client, same as above, but also causes the generate_context method to be called, which creates a context data structure, which is passed to the templates, which are then processed by the template processor. The output of that is HTML, CSS, and javascript, which is all returned back to the client in a HTTP response.
- When a user requests a report be exported on the client a 'download' request is sent to the server, generates the HTML as above, however it then converts that to PDF, data is added to both knowledge graph and RDBMS, The PDF is downloaded to the client's local machine and also stored on the server's file system.
- Compose current encounter gets data from the workitem and readings files, parses the data, and then stores all the data needed for the current encounter in a serialized file (e.g., JSON or XML) (as well as to knowledge graph on export).
- Extraction of target level summary readings
- Use of marked lesions
- Automatic lesion detection and quantification
- Extraction of lesion level readings
- Extraction of cross-section level readings
- Pathology determination
- Ontology extension
- Derivation of presentation based on nearby or related. e.g. the post-stenotic dilatation
- Natural language narrative
- Application of predictive models
- Compose other encounters gets data from the knowledge graph, stores all the data needed for the other encounter in a serialized file (e.g., JSON or XML)
- Creation of trends
- Automatic composition of key images, clinical indication, procedure, findings, impression
- Drill downs for lineal graphs of measurands along pathline
- Drill downs for cross-section readings, reference ranges, similar sections
- Natural language findings narrative generation
- Report export functionality
- DICOM SR and CDA as additional export results along with PDF
- RadLex as string source
- HL7 receiver for other predictive model input
- HL7 transmitter for export
- SPARQL endpoints for discovery research, surveillance, and other apps
- Preparation of computation models
- Reference ranges including
  - GUI for tailoring ref ranges
  - Multiple body site, age, and sex reference ranges
  - Ranges configured to troll over reference cohort to create quartiles for use as reference ranges
- Processing of technical performance to compute metrics used to construct confidence intervals
- Representation of uncertainty drawn from analytic performance calculations
- Creation of outcome prediction models to extract out data to build predication and classification models
- Provenance tracking/display
- Similar section analysis of phenotypes
- Selection of product and institution
- The CAPgraph server can also be accessed from a browser. E.g., from the browser a user can view patients who have had reports exported, view those reports as PDF, 'update' the PDF back to HTML, and re-export the updated report as a PDF.
- The Second multipart can be sent which may be reprocessed (causing the composed analysis to be tossed and regenerated, or ignored if nothing has changed)

The following references are incorporated by reference herein in their entirety for all purposes:

1. Fuchs, V. R. and H. C. Sox, Jr., Physicians' views of the relative importance of thirty medical innovations. Health Aff (Millwood), 2001. 20(5): p. 30-42.
2. Jaffer, F. A. and R. Weissleder, Molecular imaging in the clinical arena. JAMA: the journal of the American Medical Association, 2005. 293(7): p. 855-62.
3. Fleming, T. R., Surrogate endpoints and FDA's accelerated approval process. Health affairs, 2005. 24(1): p. 67-78.
4. Atkinson, A. J. e. a., Biomarkers and surrogate endpoints: preferred definitions and conceptual framework. Clinical pharmacology and therapeutics, 2001. 69(3): p. 89-95.
5. Katz, R., Biomarkers and surrogate markers: an FDA perspective. NeuroRx, 2004. 1(2): p. 189-95.
6. Lathia, C. D., et al., The value, qualification, and regulatory use of surrogate end points in drug development. Clinical pharmacology and therapeutics, 2009. 86(1): p. 32-43.
7. Creating the gene ontology resource: design and implementation. Genome Res, 2001. 11(8): p. 1425-33.
8. Ashburner, M., et al., Gene ontology: tool for the unification of biology. The Gene Ontology Consortium. Nat Genet, 2000. 25(1): p. 25-9.
9. Romero-Zaliz, R. C., et al., A Multiobjective Evolutionary Conceptual Clustering Methodology for Gene Annotation Within Structural Databases: A Case of Study on the Gene Ontology Database. IEEE Transactions on Evolutionary Computation, 2008. 12(6): p. 679-701.
10. Brazma, A., et al., Minimum information about a microarray experiment (MIAME)-toward standards for microarray data. Nat Genet, 2001. 29(4): p. 365-71.
11. Sirota, M., et al., Discovery and preclinical validation of drug indications using compendia of public gene expression data. Science translational medicine, 2011. 3(96): p. 96ra77.
12. Brown, M. S., et al., Database design and implementation for quantitative image analysis research. IEEE Trans Inf Technol Biomed, 2005. 9(1): p. 99-108.
13. Maier, D., et al., Knowledge management for systems biology a general and visually driven framework applied to translational medicine. BMC Syst Biol, 2011. 5: p. 38.

14. Sheikh, H. R., M. F. Sabir, and A. C. Bovik, A statistical evaluation of recent full reference image quality assessment algorithms. IEEE transactions on image processing: a publication of the IEEE Signal Processing Society, 2006. 15(11): p. 3440-51.
15. Toyohara, J., et al., Evaluation of 4'-[methyl-14C]thiothymidine for in vivo DNA synthesis imaging. Journal of nuclear medicine: official publication, Society of Nuclear Medicine, 2006. 47(10): p. 1717-22.
16. Yuk, S. H., et al., Glycol chitosan/heparin immobilized iron oxide nanoparticles with a tumor-targeting characteristic for magnetic resonance imaging. Biomacromolecules, 2011. 12(6): p. 2335-43.
17. Veenendaal, L. M., et al., In vitro and in vivo studies of a VEGF121/rGelonin chimeric fusion toxin targeting the neovasculature of solid tumors. Proc Natl Acad Sci USA, 2002. 99(12): p. 7866-71.
18. Wen, X., et al., Biodistribution, pharmacokinetics, and nuclear imaging studies of 111In-labeled rGel/BLyS fusion toxin in SCID mice bearing B cell lymphoma. Molecular imaging and biology: MIB: the official publication of the Academy of Molecular Imaging, 2011. 13(4): p. 721-9.
19. Wang, H. H., et al., Durable mesenchymal stem cell labelling by using polyhedral superparamagnetic iron oxide nanoparticles. Chemistry, 2009. 15(45): p. 12417-25.
20. http://www.ncbi.nlm.nih.gov/books/NBK5330/, Molecular Imaging and Contrast Agent Database (MI-CAD). 2011.
21. Zhao, B., et al., Evaluating variability in tumor measurements from same-day repeat CT scans of patients with non-small cell lung cancer. Radiology, 2009. 252(1): p. 263-72.
22. Buckler, A. J. and R. Boellaard, Standardization of quantitative imaging: the time is right, and 18F-FDG PET/CT is a good place to start. Journal of nuclear medicine: official publication, Society of Nuclear Medicine, 2011. 52(2): p. 171-2.
23. Langlotz, C. P., Enhancing the Expressiveness of Structured Reporting Systems. J. Digit. Imaging, 2000. 13: p. 49-53.
24. Liu, D., G. D. Berman, and R. N. Gray, The use of structured radiology reporting at a community hospital: A 4-year case study of more than 200,00 reports. Appl. Radiol, 2003. 32: p. 23-26.
25. Johnson, A. J., et al., Cohort Study of Structured Reporting Compared with Conventional Dictation. Radiology, 2009. 253(1): p. 74-80.
26. Langlotz, C. P., The Radiology Report: A Guide to Thoughtful Communication for Radiologists and Other Medical Professionals. 2015: Curtis P. Langlotz.
27. Dunnick, N. R. and C. P. Langlotz, The Radiology Report of the Future: A Summary of the 2007 Intersociety Conference. Journal of the American College of Radiology, 2008. 5: p. 626-629.
28. Chapman, W. W. and K. B. Cohen, Current issues in biomedical text mining and natural language processing. Journal of biomedical informatics, 2009. 42: p. 757-759.
29. Haug, P. J., D. L. Ranum, and P. R. Frederick, Computerized extraction of coded findings from free-text radiologic reports. Radiology, 1990. 174(2): p. 543-8.
30. Haug, P. J., et al., A natural language understanding system combining syntactic and semantic techniques. Proc Annu Symp Comput Appl Med Care, 1994: p. 247-51.
31. Haug, P. J., et al., A natural language parsing system for encoding admitting diagnoses. Proc AMIA Annu Fall Symp, 1997: p. 814-8.
32. Chapman, W. W., et al., Classifying free-text triage chief complaints into synddromic categories with natural language processing. Artif Intell Med, 2005. 33(1): p. 31-40.
33. Wikipedia. Natural language generation. 2017 7/26/17]; Available from: https://en.wikipedia.org/wiki/Natural-_language_generation.
34. Perera, R. and P. Nand, Recent Advances in Natural Language Generation: A Survey and Classification of the Empirical Literature. Vol. 36. 2017. 1-31.
35. Noy, N. F. M., D. L., Ontology Development 101: A Guide to Creating Your First Ontology. Stanford Knowledge Systems Laboratory technical report KSL-01-05 and Stanford Medical Informatics technical report SMI-2001-0880, 2001.
36. RSNA RadLex. Available from: http://www.rsna.org/informatics/radlex.cfm, accessed 27 November 2011.
37. Rubin, D. L., Creating and curating a terminology for radiology: ontology modeling and analysis. Journal of digital imaging: the official journal of the Society for Computer Applications in Radiology, 2008. 21(4): p. 355-62.
38. Buckler, A. J., et al., Quantitative imaging biomarker ontology (QIBO) for knowledge representation of biomedical imaging biomarkers. Journal of digital imaging: the official journal of the Society for Computer Applications in Radiology, 2013. 26(4): p. 630-41.
39. Freimuth, R. R., et al., Life sciences domain analysis model. J Am Med Inform Assoc, 2012. 19(6): p. 1095-102.
40. Buckler, A., et al., A Novel Knowledge Representation Framework for the Statistical Validation of Quantitative Imaging Biomarkers. Journal of Digital Imaging, 2013. 26(4): p. 614-629.
41. Sheahan, M., et al., Non-invasive Quantitative Assessment of Atherosclerotic Plaque Tissue Characteristics with Software-Aided Measurements from Standard CTA. Radiology, 2017. in press.
42. Gupta, A., et al., Semi-Automated Detection of High-Risk Atherosclerotic Carotid Artery Plaque Features from Computed Tomography Angiography, in European Stroke Conference. 2017: Berlin.
43. St Pierre, S., et al., Measurement Accuracy of Atherosclerotic Plaque Structure on CT Using Phantoms to Establish Ground Truth. Acad Radiol, 2017.
44. Keith, J. J., A. Buckler, and J. Hamilton, Development of vascuCAP, an MR Image analysis system for longitudinal surveillance of cardiovascular disease in women who developed preclampsia. Pregnancy Hypertension: An International Journal of Women's Cardiovascular Health, 2014. 4(4).
45. Buckler, A. J. and J. C. Keith, Advanced Biomarkers. European Biopharmaceutical Review, 2014: p. 10-14.
46. Buckler, A. J., et al., Non-invasive Theranostic to Predict and Assess Response to Atherosclerotic Drugs, in Experimental Biology. 2013: Boston.
47. Wan, T., et al., Spatio-temporal texture (SpTeT) for distinguishing vulnerable from stable atherosclerotic plaque on dynamic contrast enhancement (DCE) Mill in a rabbit model. Medical Physics, 2014. 41 (April 2014).
48. Organization, W. H., The Atlas of Heart Disease and Stroke. 2014.
49. Misra, A. and U. Shrivastava, Obesity and Dyslipidemia in South Asians. Nutrients, 2013. 5(7): p. 2708-2733.

50. Wang, J., et al., Nutrition, Epigenetics, and Metabolic Syndrome. Antioxidants & Redox Signaling, 2011. 17(2): p. 282-301.
51. Kaur, J., A Comprehensive Review on Metabolic Syndrome. Cardiology Research and Practice, 2014. 2014: p. 21.
52. May, J. M., et al., Low-Risk Patients With Chest Pain in the Emergency Department: Negative 64-MDCT Coronary Angiography May Reduce Length of Stay and Hospital Charges. American Journal of Roentgenology, 2009. 193(1): p. 150-154.
53. Hoffmann, U., et al., Coronary Computed Tomography Angiography for Early Triage of Patients With Acute Chest Pain: The ROMICAT (Rule Out Myocardial Infarction using Computer Assisted Tomography) Trial. J Am Coll Cardiol, 2009. 53(18): p. 1642-1650.
54. Goldstein, J. A., et al., The CT-STAT (Coronary Computed Tomographic Angiography for Systematic Triage of Acute Chest Pain Patients to Treatment) Trial. J Am Coll Cardiol, 2011. 58(14): p. 1414-1422.
55. Hoffmann, U., et al., Coronary CT Angiography versus Standard Evaluation in Acute Chest Pain. N Engl J Med, 2012. 367(4).
56. Litt, H. I., et al., CT Angiography for Safe Discharge of Patients with Possible Acute Coronary Syndromes. N Engl J Med, 2012. 366(15): p. 1393-403.
57. Barnett, H. J., et al., Benefit of carotid endarterectomy in patients with symptomatic moderate or severe stenosis. North American Symptomatic Carotid Endarterectomy Trial Collaborators. N Engl J Med, 1998. 339(20): p. 1415-25.
58. Group, E. C. S. T. C., Randomised trial of endarterectomy for recently symptomatic carotid stenosis: final results of the MRC European Carotid Surgery Trial (ECST). The Lancet, 1998. 351(9113): p. 1379-1387.
59. Meier, P., et al., Short term and intermediate term comparison of endarterectomy versus stenting for carotid artery stenosis: systematic review and meta-analysis of randomised controlled clinical trials. Bmj, 2010. 340 (feb12 1): p. c467-c467.
60. Ederle, J., et al., Carotid artery stenting compared with endarterectomy in patients with symptomatic carotid stenosis (International Carotid Stenting Study): an interim analysis of a randomised controlled trial. Lancet, 2010. 375(9719): p. 985-97.
61. Underhill, H. R., et al., Arterial remodeling in subclinical carotid artery disease. JACC Cardiovasc Imaging, 2009. 2(12): p. 1381-9.
62. Delaney, J. C., et al., Effect of inter-reader variability on outcomes in studies using carotid intima media thickness quantified by carotid ultrasonography. European Journal of Epidemiology, 2010. 25(6): p. 385-392.
63. Fernandez-Friera, L., et al., Prevalence, Vascular Distribution, and Multiterritorial Extent of Subclinical Atherosclerosis in a Middle-Aged Cohort: The PESA (Progression of Early Subclinical Atherosclerosis) Study. Circulation, 2015. 131(24): p. 2104-13.
64. Magge, R., et al., Clinical Risk Factors and CT Imaging Features of Carotid Atherosclerotic Plaques as Predictors of New Incident Carotid Ischemic Stroke: A Retrospective Cohort Study. American Journal of Neuroradiology, 2013. 34(2): p. 402-409.
65. Evans, M. R., et al., Carotid atherosclerosis predicts incident acute coronary syndromes in rheumatoid arthritis. Arthritis & Rheumatism, 2011. 63(5): p. 1211-1220.
66. van't Klooster, R., et al., Visualization of Local Changes in Vessel Wall Morphology and Plaque Progression in Serial Carotid Artery Magnetic Resonance Imaging. Stroke, 2014. 45(8): p. e160-e163.
67. Mani, V., et al., Predictors of change in carotid atherosclerotic plaque inflammation and burden as measured by 18-FDG-PET and MRI, respectively, in the dal-PLAQUE study. Int J Cardiovasc Imaging, 2014. 30(3): p. 571-582.
68. Lei-xing, X., et al., Combined application of 18F-fluorodeoxyglucose positron emission tomography/computed tomography and magnetic resonance imaging in early diagnosis of vulnerable carotid atherosclerotic plaques. Journal of International Medical Research, 2014. 42(1): p. 213-223.
69. Tawakol, A., et al., Intensification of Statin Therapy Results in a Rapid Reduction in Atherosclerotic Inflammation: Results of a Multicenter Fluorodeoxyglucose-Positron Emission Tomography/Computed Tomography Feasibility Study. J Am Coll Cardiol, 2013. 62(10): p. 909-917.
70. Underhill, H. R., et al., A noninvasive imaging approach to assess plaque severity: the carotid atherosclerosis score. AJNR Am J Neuroradiol, 2010. 31(6): p. 1068-75.
71. Watanabe, Y. and M. Nagayama, MR plaque imaging of the carotid artery. Neuroradiology, 2010. 52(4): p. 253-74.
72. Sanak, D., et al., The role of magnetic resonance imaging for acute ischemic stroke. Biomed Pap Med Fac Univ Palacky Olomouc Czech Repub, 2009. 153(3): p. 181-7.
73. Kawahara, I., et al., The detection of carotid plaque rupture caused by intraplaque hemorrhage by serial high-resolution magnetic resonance imaging: a case report. Surg Neurol, 2008. 70(6): p. 634-9; discussion 639.
74. Saam, T., et al., The vulnerable, or high-risk, atherosclerotic plaque: noninvasive MR imaging for characterization and assessment. Radiology, 2007. 244(1): p. 64-77.
75. Cappendijk, V. C., et al., Assessment of human atherosclerotic carotid plaque components with multisequence MR imaging: initial experience. Radiology, 2005. 234(2): p. 487-92.
76. Yuan, C., et al., Carotid atherosclerotic plaque: noninvasive MR characterization and identification of vulnerable lesions. Radiology, 2001. 221(2): p. 285-99.
77. Qureshi, A. I., et al., Guidelines for screening of extracranial carotid artery disease: a statement for healthcare professionals from the multidisciplinary practice guidelines committee of the American Society of Neuroimaging; cosponsored by the Society of Vascular and Interventional Neurology. J Neuroimaging, 2007. 17(1): p. 19-47.
78. Fuster, V. and P. R. Moreno, Atherothrombosis as a systemic, often silent, disease. Nat Clin Pract Cardiovasc Med, 2005. 2(9): p. 431.
79. Horie, N., et al., Assessment of Carotid Plaque Stability Based on the Dynamic Enhancement Pattern in Plaque Components With Multidetector CT Angiography. Stroke, 2012. 43(2): p. 393-398.
80. ten Kate, G. L., et al., Noninvasive Imaging of the Vulnerable Atherosclerotic Plaque. Current problems in cardiology, 2010. 35(11): p. 556-591.
81. Wintermark, M., et al., High-Resolution CT Imaging of Carotid Artery Atherosclerotic Plaques. American Journal of Neuroradiology, 2008. 29(5): p. 875-882.
82. Wintermark, M., et al., Carotid Plaque CT Imaging in Stroke and Non-Stroke Patients. Annals of neurology, 2008. 64(2): p. 149-157.
83. de Weert, T. T., et al., In Vivo Characterization and Quantification of Atherosclerotic Carotid Plaque Components With Multidetector Computed Tomography and 84. Zavodni, A. E. H., et al., Carotid Artery Plaque Morphology and Composition in Relation to Incident Cardiovascular Events: The Multi-Ethnic Study of Atherosclerosis (MESA). Radiology, 2014. 271(2): p. 381-389.
85. Varma, N., et al., Coronary Vessel Wall Contrast Enhancement Imaging as a Potential Direct Marker of Coronary Involvement Integration of Findings From CAD and SLE Patients. JACC: Cardiovascular Imaging, 2014. 7(8): p. 762-770.
86. Kerwin, W. S., et al., Mill of Carotid Atherosclerosis. American Journal of Roentgenology, 2013. 200(3): p. W304-W313.
87. Bourque, J. M., et al., Usefulness of Cardiovascular Magnetic Resonance Imaging of the Superficial Femoral Artery for Screening Patients With Diabetes Mellitus for Atherosclerosis. Am J Cardiol, 2012. 110(1): p. 50-56.
88. Glagov, S., et al., Compensatory enlargement of human atherosclerotic coronary arteries. N Engl J Med, 1987. 316(22): p. 1371-5.
89. Hardie, A. D., et al., The impact of expansive arterial remodeling on clinical presentation in carotid artery disease: a multidetector CT angiography study. AJNR Am J Neuroradiol, 2007. 28(6): p. 1067-70.
90. Gupta, A., et al., Carotid plaque Mill and stroke risk: a systematic review and meta-analysis. Stroke, 2013. 44(11): p. 3071-7.
91. Sundaram, B., et al., Anatomy and Terminology for the Interpretation and Reporting of Cardiac MDCT: Part 1, Structured Report, Coronary Calcium Screening, and Coronary Artery Anatomy. AJR Am J Roentgenol, 2008. 192: p. 574-583.
92. Kwee, R. M., Systematic review on the association between calcification in carotid plaques and clinical ischemic symptoms. Journal of vascular surgery, 2010. 51(4): p. 1015-1025.
93. Ross, G., Too Few Americans Take Statins, CDC Study Reveals. American Council on Science and Health, 2015.
94. Sabatine, M. S., et al., Evolocumab and Clinical Outcomes in Patients with Cardiovascular Disease. New England Journal of Medicine, 2017. 376(18): p. 1713-1722.
95. Taylor, P. In light of Fourier data, what future for Alnylam and TMC's PCSK9 inclisiran? 2017.
96. W3C. Resource Description Framework (RDF). 2013; Available from: https://www.w3.org/2001/sw/#rdf.
97. Wikipedia. Relational database management system. 2017; Available from: https://en.wikipedia.org/wiki/Relational_database_management_system.
98. Wikipedia. Unified Modeling Language. 2017; Available from: https://en.wikipedia.org/wiki/Unified_Modeling_Language.
99. Liu, T., et al., The Imaging Biomarker Ontology: Ontology-based Support for Imaging Biomarker Research, in Society for Imaging Informatics in Medicine 2011 Annual Meeting. 2011.
100. Noy, N. F. and D. L. McGuinness, A Guide to Creating Your First Ontology. Stanford Knowledge Systems Laboratory technical report KSL-01-05 and Stanford Medical Informatics technical report SMI-2001-0880, 2001.
101. Services, U.S.D.o.H.H. Health Information Privacy. 2017; Available from: https://www.hhs.gov/hipaa/index.html/.
102. SPARQL, a query language and protocol for RDF access released by the W3C RDF Data Access Working Group. Available from: http://www.w3.org/wiki/SparqlImplementations, accessed 27 Nov. 2011.
103. Wikipedia. Hypertext Transfer Protocol. 2017; Available from: https://en.wikipedia.org/wiki/Hypertext_Transfer_Protocol.
104. Foundation, D. S. Django Project. 2017 7/26/2017]; Available from: https://www.djangoproject.com/.
105. W3C. About W3C: HTML. 2017; Available from: https://www.w3.org/html/.
106. Wikipedia. Cascading Style Sheets. 2017; Available from: https://en.wikipedia.org/wiki/Cascading_Style_Sheets.
107. Javascript. 2017; Available from: https://www.javascript.com/.
108. Incorporated, A. S. PDF. Three letters that changed the world. 2017; Available from: https://acrobat.adobe.com/us/en/why-adobe/about-adobe-pdf.html.
109. Union, S. Stardog. 2017; Available from: http://www.stardog.com/.
110. Corporation, O. MySQL. 2017; Available from: https://www.mysql.com/.
111. Frederiksen, B. Python knowledge engine. 2010; Available from: http://pyke.sourceforge.net/.
112. GitHub. simplenlg. 2017; Available from: https://github.com/simplenlg/simplenlg.
113. Solomon, H. DICOM Structured Reporting Overview. in RSNA Industry Forum on Structured Reporting http://reportingwiki.rsna.org/images/0/00/RSNA_Reporting_Forum_Solomon.pdf.
114. Regenstrief Institute, I. LOINC from Regenstrief 2017; Available from: https://loinc.org/.
115. SNOMED Clinical Terms® (SNOMED CT®). Available from: http://www.gov/research/umls/Snomed/snomed_main.html, accessed 27 Nov. 2011.
116. Rubin, D. L., et al., iPad: Semantic annotation and markup of radiological images. AMIA . . . Annual Symposium proceedings/AMIA Symposium. AMIA Symposium, 2008: p. 626-30.
117. Wikipedia. Extensible Markup Language. 2017; Available from: https://en.wikipedia.org/wiki/XML.
118. Wikipedia. Health Level 7. 2017; Available from: https://en.wikipedia.org/wiki/Health_Level_7.
119. Wikipedia. Clinical Document Architecture. 2017; Available from: https://en.wikipedia.org/wiki/Clinical_Document_Architecture.
120. Foundation, P. S. Python. 2017; Available from: https://www.python.org/.
121. Spronk, R. Minimal Lower Layer Protocol. 2003; Available from: http://www.hl7.org/documentcenter/public_temp_F76F3B66-1C23-BA17-0CA36A6C00D227F6/wg/inm/mllp_transport_specification.PDF.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

The invention claimed is:

1. A system comprising a processor and a non-transient storage medium, the storage medium including processor executable instructions implementing a report generation module include a natural language generator, the report generation module configured to:
receive a data set including non-invasive quantitative and objective measurements of one or more biological properties of a patient;
determining anatomical field of views relating to the patient based on the data set, wherein the anatomical field of views include a target, a vessel, and a cross-section level block;
determining one or more pathologies for the patient based on the anatomical field of views and one or more predetermined rules;
process the data set using the natural language generator to automatically provide a natural language narrative including an objectively structured set of a plurality of findings based on the quantitative and objective measurements and wherein the natural language narrative includes the one or more predetermined rules as grammatical elements; and
generate and display a report for the patient, the report including the natural language narrative.

2. The system of claim 1, wherein the generated report is configured to correlate each of the plurality of findings in the natural language narrative with a specific quantitative data subset supporting that finding.

3. The system of claim 2, wherein the generated report further includes a user interface configured to enable a user to selectively view the specific quantitative data subset correlated with each of the findings in the natural language narrative.

4. The system of claim 1, wherein the data set includes a hierarchical data structure including one or more qualitative pathological features which are determined based on the quantitative and objective measurements of the one or more biological properties.

5. The system of claim 4, wherein the natural language narrative includes an objective natural language interpretation of both the quantitative and objective measurements and the qualitative pathological features.

6. The system of claim 5, wherein the qualitative pathological features include phenotype classification for a pathology.

7. The system of claim 4, wherein the hierarchical data structure further includes one or more predictive outcomes for a pathology.

8. The system of claim 7, wherein the natural language narrative includes an objective natural language interpretation of the one or more predictive outcomes for the pathology.

9. A system comprising a processor and a non-transient storage medium, the storage medium including processor executable instructions implementing a report generation module, the report generation module configured to:
receive a data set including non-invasive quantitative and objective measurements of one or more biological properties of a patient;
determining anatomical field of views relating to the patient based on the data set, wherein the anatomical field of views include a target, a vessel, and a cross-section level block;
determining one or more pathologies for the patient based on the anatomical field of views and one or more predetermined rules; and
use an ontological data model based on the one or more predetermined rules including a taxonomic hierarchy of biomedical concepts related to a domain of biological properties to analyze the data set and generate and display a report for the patient based on ontology from the ontological data model.

10. The system of claim 9, wherein the report includes longitudinal trend analysis based on ontology from ontological data model.

11. The system of claim 10, wherein longitudinal trend analysis includes using pre-computed data points and information for a trend from older data sets to reduce processing time.

12. The system of claim 9, wherein the report utilizes pre-computed data points and information from older data sets to reduce processing time.

13. The system of claim 9, wherein the ontological data model includes semantic relationships between biomedical concepts.

14. The system of claim 9, wherein the quantitative and objective measurements include imaging data.

15. The system of claim 9, wherein the taxonomic hierarchy of biomedical concepts includes a hierarchical characterization of a target anatomical site.

16. The system of claim 15, wherein the hierarchical characterization of the target anatomical site includes characterization of a vessel, a vessel segment, and a segment cross-section.

17. The system of claim 16, wherein the hierarchical characterization of the target anatomical site further includes a characterization of an anatomic region for the vessel.

18. The system of claim 9, wherein the ontological data model includes defines relationships between qualitative pathological features and quantitative and objective measurements of one or more biological properties.

19. The system of claim 18, wherein the report includes one or more qualitative pathological features for the patient which are automatically and objectively determined based on the ontological data model.

20. The system of claim 19, wherein the one or more qualitative pathological features include phenotype classification for a pathology.

21. The system of claim 19, wherein the one or more qualitative pathological features provide for computer aided detection of a pathology.

22. The system of claim 9, wherein the system includes a client server architecture, wherein the server is configured to receive a request from a client whereby such request triggers the generation of the report.

23. The system of claim 22, wherein the server is configured to work ahead and pre-compute available report information prior to receiving a client request to reduce processing time.

* * * * *

UNITED STATES PATENT AND TRADEMARK OFFICE
CERTIFICATE OF CORRECTION

| | | |
|---|---|---|
| PATENT NO. | : 11,257,584 B2 | Page 1 of 1 |
| APPLICATION NO. | : 16/102042 | |
| DATED | : February 22, 2022 | |
| INVENTOR(S) | : Mary E. Buckler et al. | |

It is certified that error appears in the above-identified patent and that said Letters Patent is hereby corrected as shown below:

In the Specification

In Column 1, Line 16, please insert the following:
--GOVERNMENT RIGHTS IN THE INVENTION
This invention was made with government support under National Institute of Health SBIR Award R44 HL126224 awarded by the National Institute of Health. The government may have certain rights in the invention.--

Signed and Sealed this
Twenty-first Day of February, 2023

Katherine Kelly Vidal

Katherine Kelly Vidal
*Director of the United States Patent and Trademark Office*